US012322492B2

(12) United States Patent
Abraham et al.

(10) Patent No.: US 12,322,492 B2
(45) Date of Patent: Jun. 3, 2025

(54) PERSONALIZED EVENT DETECTION

(71) Applicant: Medtronic MiniMed, Inc., Northridge, CA (US)

(72) Inventors: Sinu Bessy Abraham, Georgetown, TX (US); Chantal M. McMahon, Atlanta, GA (US); Pratik J. Agrawal, Stevenson Ranch, CA (US); Boyi Jiang, Pasadena, CA (US); Yuxiang Zhong, Arcadia, CA (US); Michael P. Stone, Long Beach, CA (US); Huzefa F. Neemuchwala, Simi Valley, CA (US)

(73) Assignee: MEDTRONIC MINIMED, INC., Northridge (CA)

( * ) Notice: Subject to any disclaimer, the term of this patent is extended or adjusted under 35 U.S.C. 154(b) by 0 days.

(21) Appl. No.: 18/749,277

(22) Filed: Jun. 20, 2024

(65) Prior Publication Data

US 2024/0339196 A1    Oct. 10, 2024

Related U.S. Application Data

(63) Continuation of application No. 17/652,816, filed on Feb. 28, 2022, now Pat. No. 12,057,214, which is a
(Continued)

(51) Int. Cl.
*A61B 5/00* (2006.01)
*A61M 5/172* (2006.01)
(Continued)

(52) U.S. Cl.
CPC ........... *G16H 20/60* (2018.01); *A61B 5/4839* (2013.01); *A61B 5/7225* (2013.01);
(Continued)

(58) Field of Classification Search
CPC ... A61B 5/4839; A61B 5/7225; A61B 5/7275; A61B 5/743; A61B 5/14532;
(Continued)

(56) References Cited

U.S. PATENT DOCUMENTS

| | | |
|---|---|---|
| 3,631,847 A | 1/1972 | Hobbs, II |
| 4,212,738 A | 7/1980 | Henne |

(Continued)

FOREIGN PATENT DOCUMENTS

| | | |
|---|---|---|
| CN | 104520862 A | 4/2015 |
| DE | 4329229 A1 | 3/1995 |

(Continued)

OTHER PUBLICATIONS

Shaw, G. W. et al., "In Vitro Testing of a Simply Constructed, Highly Stable Glucose Sensor Suitable for Implantation in Diabetic Patients", Biosensors and Bioelectronics, 1991, vol. 6, No. 5, pp. 401-406.

(Continued)

*Primary Examiner* — Phillip A Gray
(74) *Attorney, Agent, or Firm* — Weaver Austin Villeneuve & Sampson LLP

(57) ABSTRACT

Techniques for detection of occurrence of a meal are provided. In some embodiments, the techniques may involve obtaining a plurality of glucose measurements indicative of a glucose level in a body of a patient during an analysis interval. The techniques may involve determining one or more glucose measurement statistics based on the plurality of glucose measurements. The techniques may involve determining a likelihood of the patient having consumed a meal during the analysis interval based on the one or more glucose measurement statistics that are correlative to an occurrence of a meal for the patient. The techniques may involve detecting an occurrence of the meal during the (Continued)

analysis interval based on the likelihood of the patient having consumed the meal during the analysis interval.

20 Claims, 15 Drawing Sheets

Related U.S. Application Data continuation of application No. 16/579,651, filed on Sep. 23, 2019, now abandoned, which is a continuation of application No. 15/240,711, filed on Aug. 18, 2016, now Pat. No. 10,463,297.

(60) Provisional application No. 62/329,021, filed on Apr. 28, 2016, provisional application No. 62/304,618, filed on Mar. 7, 2016, provisional application No. 62/304,615, filed on Mar. 7, 2016, provisional application No. 62/304,609, filed on Mar. 7, 2016, provisional application No. 62/304,605, filed on Mar. 7, 2016, provisional application No. 62/286,828, filed on Jan. 25, 2016, provisional application No. 62/266,820, filed on Dec. 14, 2015, provisional application No. 62/208,479, filed on Aug. 21, 2015.

(51) Int. Cl.
*G06N 7/01* (2023.01)
*G16H 20/17* (2018.01)
*G16H 20/60* (2018.01)
*G16H 50/20* (2018.01)
*A61B 5/145* (2006.01)

(52) U.S. Cl.
CPC ............ *A61B 5/7275* (2013.01); *A61B 5/743* (2013.01); *A61M 5/1723* (2013.01); *G06N 7/01* (2023.01); *G16H 20/17* (2018.01); *G16H 50/20* (2018.01); *A61B 5/14532* (2013.01); *A61M 2205/3584* (2013.01); *A61M 2205/50* (2013.01); *A61M 2205/502* (2013.01)

(58) Field of Classification Search
CPC ................ G16H 50/20; A61M 5/1723; A61M 2205/3584; A61M 2205/50; A61M 2205/502; G06F 19/3468; G06N 7/005
USPC .......................................................... 604/66
See application file for complete search history.

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | DeCant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,755,173 A | 7/1988 | Konopka et al. |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,497,772 A | 3/1996 | Schulman et al. |
| 5,505,709 A | 4/1996 | Funderburk et al. |
| 5,522,803 A | 6/1996 | Teissen-Simony |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Iliff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,807,375 A | 9/1998 | Gross et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach |
| 5,868,669 A | 2/1999 | Iliff |

(56) References Cited

U.S. PATENT DOCUMENTS

| | | |
|---|---|---|
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,954,643 A | 9/1999 | Vanantwerp et al. |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,017,328 A | 1/2000 | Fischell et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,259,937 B1 | 7/2001 | Schulman et al. |
| 6,329,161 B1 | 12/2001 | Heller et al. |
| 6,355,021 B1 | 3/2002 | Nielsen et al. |
| 6,379,301 B1 | 4/2002 | Worthington et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,544,212 B2 | 4/2003 | Galley et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,589,229 B1 | 7/2003 | Connelly et al. |
| 6,591,125 B1 | 7/2003 | Buse et al. |
| 6,591,876 B2 | 7/2003 | Safabash |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,736,797 B1 | 5/2004 | Larsen et al. |
| 6,740,072 B2 | 5/2004 | Starkweather et al. |
| 6,746,582 B2 | 6/2004 | Heller et al. |
| 6,747,556 B2 | 6/2004 | Medema et al. |
| 6,749,587 B2 | 6/2004 | Flaherty |
| 6,749,740 B2 | 6/2004 | Liamos et al. |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,809,653 B1 | 10/2004 | Mann et al. |
| 6,817,990 B2 | 11/2004 | Yap et al. |
| 6,827,702 B2 | 12/2004 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,153,263 B2 | 12/2006 | Carter et al. |
| 7,153,289 B2 | 12/2006 | Vasko |
| 7,303,549 B2 | 12/2007 | Flaherty et al. |
| 7,323,142 B2 | 1/2008 | Pendo et al. |
| 7,396,330 B2 | 7/2008 | Banet et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |

(56) References Cited

U.S. PATENT DOCUMENTS

| | | |
|---|---|---|
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente, IV et al. |
| 8,674,288 B2 | 3/2014 | Hanson et al. |
| 10,391,242 B2 | 8/2019 | Agrawal et al. |
| 10,463,297 B2 | 11/2019 | Abraham et al. |
| 10,664,569 B2 | 5/2020 | McMahon et al. |
| 10,867,012 B2 | 12/2020 | Agrawal et al. |
| 12,057,214 B2 | 8/2024 | Abraham et al. |
| 2001/0044731 A1 | 11/2001 | Coffman et al. |
| 2002/0013518 A1 | 1/2002 | West et al. |
| 2002/0055857 A1 | 5/2002 | Mault |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon |
| 2005/0154271 A1 | 7/2005 | Rasdal et al. |
| 2005/0192557 A1 | 9/2005 | Brauker et al. |
| 2006/0031094 A1 | 2/2006 | Cohen et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0123819 A1 | 5/2007 | Mernoe et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |
| 2010/0160861 A1 | 6/2010 | Causey, III et al. |
| 2013/0338630 A1 | 12/2013 | Agrawal et al. |
| 2015/0057634 A1 | 2/2015 | Mastrototaro et al. |
| 2015/0057807 A1 | 2/2015 | Mastrototaro et al. |
| 2015/0190098 A1 | 7/2015 | Patek et al. |
| 2015/0328402 A1 | 11/2015 | Nogueira et al. |
| 2017/0053072 A1 | 2/2017 | Agrawal et al. |
| 2017/0053084 A1 | 2/2017 | McMahon et al. |
| 2017/0053552 A1 | 2/2017 | Zhong et al. |
| 2020/0015739 A1 | 1/2020 | Abraham et al. |
| 2022/0181003 A1 | 6/2022 | Abraham et al. |

FOREIGN PATENT DOCUMENTS

| | | |
|---|---|---|
| EP | 0319268 A2 | 6/1989 |
| EP | 0806738 A1 | 11/1997 |
| EP | 0880936 A2 | 12/1998 |
| EP | 1338295 A1 | 8/2003 |
| EP | 1631036 A2 | 3/2006 |
| GB | 2218831 A | 11/1989 |
| WO | 9620745 A1 | 7/1996 |
| WO | 9636389 A1 | 11/1996 |
| WO | 9637246 A1 | 11/1996 |
| WO | 9721456 A1 | 6/1997 |
| WO | 9820439 A1 | 5/1998 |
| WO | 9824358 A2 | 6/1998 |
| WO | 9842407 A1 | 10/1998 |
| WO | 9849659 A2 | 11/1998 |
| WO | 9859487 A1 | 12/1998 |
| WO | 9908183 A1 | 2/1999 |
| WO | 9910801 A1 | 3/1999 |
| WO | 9918532 A1 | 4/1999 |
| WO | 9922236 A1 | 5/1999 |
| WO | 0010628 A2 | 3/2000 |
| WO | 0019887 A1 | 4/2000 |
| WO | 0048112 A2 | 8/2000 |
| WO | 02058537 A2 | 8/2002 |
| WO | 02066101 A2 | 8/2002 |
| WO | 03001329 A2 | 1/2003 |
| WO | 03094090 A2 | 11/2003 |
| WO | 2005065538 A2 | 7/2005 |
| WO | 2013032965 A1 | 3/2013 |

OTHER PUBLICATIONS

Shichiri, M., "A Needle-Type Glucose Sensor—A Valuable Tool Not Only for a Self-Blood Glucose Monitoring but for a Wearable Artifiical Pancreas", Life Support Systems Proceedings, XI Annual Meeting ESAO, Alpbach-Innsbruck, Austria, Sep. 1984, pp. 7-9.

Shichiri, M. et al., "An Artificial Endocrine Pancreas-problems Awaiting Solution for Long-term Clinical Applications of a Glucose Sensor", Frontiers of Medical and Biological Engineering : the International Journal of the Japan Society of Medical Electronics and Biological Engineering, 1991, vol. 3, No. 4, pp. 283-292.

Shichiri, M. et al., "Closed-loop Glycemic Control With a Wearable Artificial Endocrine Pancreas. Variations in Daily Insulin Requirements to Glycemic Response", Diabetes, Dec. 1984, vol. 33, No. 12, pp. 1200-1202.

Shichiri, M. et al., "Glycaemic Control in Pancreatectomized Dogs With a Wearable Artificial Endocrine Pancreas", Diabetologia, Mar. 1983, vol. 24, No. 3, pp. 179-184.

Shichiri, M. et al., "In Vivo Characteristics of Needle-type Glucose Sensor-measurements of Subcutaneous Glucose Concentrations in Human Volunteers", Hormone and Metabolic Research. Supplement Series, 1988, vol. 20, pp. 17-20.

Shichiri, M. et al., "Membrane Design for Extending the Long-Life of an Implantable Glucose Sensor," Diabetes Nutrition and Metabolism, 1989, vol. 2, No. 4, pp. 309-313.

Shichiri, M. et al., "Normalization of the Paradoxic Secretion of Glucagon in Diabetics Who Were Controlled by the Artificial Beta Cell", Diabetes, Apr. 1979, vol. 28, No. 4, pp. 272-275.

Shichiri, M. et al., "Telemetry Glucose Monitoring Device With Needle-type Glucose Sensor: a Useful Tool for Blood Glucose Monitoring in Diabetic Individuals", Diabetes care, May-Jun. 1986, vol. 9, No. 3, pp. 298-301.

Shichiri, M. et al., "The Wearable Artificial Endocrine Pancreas with a Needle-Type Glucose Sensor: Perfect Glycemic Control in Ambulatory Diabetes," Acta Paediatrica Japonica, 1984, vol. 26, No. 3, pp. 359-370.

Shichiri, M. et al., "Wearable Artificial Endocrine Pancrease With Needle-type Glucose Sensor", Lancet, Nov. 1982, vol. 2, No. 8308, pp. 1129-1131.

Shinkai.S et al., "Molecular Recognition of Mono- and Di-Saccharides by Phenylboronic Acids in Solvent Extraction and as a Monolayer", Journal of the Chemical Society Chemical Communications, Aug. 1991, vol. 15,No. 15, pp. 1039-1041.

Shults, M. C., "A Telemetry-Instrumentation System for Monitoring Multiple Subcutaneously Implanted Glucose Sensors", IEEE Transactions on Bio-medical Engineering, Oct. 1994, vol. 41, No. 10, pp. 937-942.

Sternberg, R. et al., "Study and Development of Multilayer Needle-type Enzyme-based Glucose Microsensors", Biosensors, 1989, vol. 4, pp. 27-40.

(56) References Cited

OTHER PUBLICATIONS

Strowig, S. M., "Initiation and Management of Insulin Pump Therapy", The Diabetes Educator, Feb. 1993, vol. 19, No. 1, pp. 50-60.
Tamiya, E. et al., "Micro Glucose Sensors using Electron Mediators Immobilized on a Polypyrrole-Modified Electrode", Sensors and Actuators, 1989, vol. 18, pp. 297-307.
Urban, G., et al., "Miniaturized Multi-enzyme Biosensors Integrated With Ph Sensors on Flexible Polymer Carriers for in Vivo Applications", Biosensors Bioelectronics, 1992, vol. 7, pp. 733-739.
Urban, G., et al., "Miniaturized Thin-film Biosensors Using Covalently Immobilized Glucose Oxidase", Biosensors Bioelectronics, 1991, vol. 6, pp. 555-562.
U.S. Final Office Action dated Jan. 28, 2019, in U.S. Appl. No. 15/240,711.
U.S. Non-Final Office Action dated Dec. 7, 2023 in U.S. Appl. No. 17/652,816.
U.S. Non-Final Office Action dated Jun. 15, 2018, in U.S. Appl. No. 15/240,711.
U.S. Non-Final Office Action dated Nov. 26, 2021, in U.S. Appl. No. 16/579,651.
U.S. Notice of Allowance dated Jun. 26, 2019 in U.S. Appl. No. 15/240,711.
U.S. Notice of Allowance dated Mar. 21, 2024 in U.S. Appl. No. 17/652,816.
Velho, G., et al., "In Vivo Calibration of a Subcutaneous Glucose Sensor for Determination of Subcutaneous Glucose Kinetics", Diab. Nutr. Metab., 1988, vol. 3, pp. 227-233.
Wang, J. et al., "Needle-type Dual Microsensor for the Simultaneous Monitoring of Glucose and Insulin", Analytical Chemistry, Feb. 15, 2001, vol. 73, No. 4, pp. 844-847.
Yamasaki, Y. et al., "Direct Measurement of Whole Blood Glucose by a Needle-type Sensor", Clinica Chimica Acta; International Journal of Clinical Chemistry, Mar. 15, 1989, vol. 180, No. 1, pp. 93-98.
Yokoyama, K. et al., "Integrated Biosensor for Glucose and Galactose", Analytica Chimica Acta, 1989, vol. 218, pp. 137-142.
CA Office Action dated Sep. 26, 2024 in CA Application No. 2994723.
Abel, P. et al., "Experience With an Implantable Glucose Sensor as a Prerequisite of an Artificial Beta Cell", Biomed Biochim Acta, 1984, vol. 43, No. 5, pp. 577-584.
Bindra, D.S. et al., "Design and in Vitro Studies of a Needle-type Glucose Sensor for Subcutaneous Monitoring", American Chemistry Society, Sep. 1991, vol. 63, No. 17, pp. 1692-1696.
Bode, B.W. et al., "Reduction in Severe Hypoglycemia With Long-term Continuous Subcutaneous Insulin Infusion in Type I Diabetes", Diabetes Care, Apr. 1996, vol. 19, No. 4, pp. 324-327.
Bode., et al., "Pumping Protocol—A Guide to Insulin Pump Therapy Initiation," from Medtronic—Medical Education Academia, Jun. 2010, pp. 40 pages.
Boguslavsky, L. et al., "Applications of Redox Polymers in Biosensors", Solid State Ionics, Mar. 1993, vol. 60, No. 1-3, pp. 189-197.
Cameron F, et al., "Probabilistic Evolving Meal Detection and Estimation of Meal Total Glucose Appearance Author Affiliations", Journal of Diabetes Science and Technology Volume Diabetes Technology Society, 2009, vol. 3(5), pp. 1022-1030.
Disetronic H-TRON® plus Quick Start Manual, 91 pages, [pre-2012].
Disetronic H-TRON plus Reference Manual, 83 pages, [pre-2012].
Disetronic My Choice H-TRON plus Insulin Pump Reference Manual, 102 pages, [pre-2012].
Disetronic My Choice. TM D-TRONTM Insulin Pump Reference Manual, 162 pages, [pre-2012].
Examiner's Requisition from counterpart Canadian Application No. 2994723 dated Oct. 18, 2022, 5 pp.
Facchinetti A., et al., "Reconstruction of Glucose in Plasma From Interstitial Fluid Continuous Glucose Monitoring Data: Role of Sensor Calibration," Journal of Diabetes Science and Technology, 2007, vol. 1(5), pp. 617-623.
First Office Action and Search Report from counterpart Chinese Application No. 201680055490.2 dated Dec. 9, 2021, 20 pp.
Geise, R.J. et al., "Electropolymerized 1,3-Diaminobenzene for the Construction of a 1,1'-Dimethylferrocene Mediated Glucose Biosensor", Analytica Chimica Acta, Sep. 1993, vol. 281, No. 3, pp. 467-473.
Gernet, S. et al., "A Planar Glucose Enzyme Electrode", Sensors and Actuators, May 1989, vol. 17, No. 3-4, pp. 537-540.
Gernet, S. et al., "Fabrication and Characterization of a Planar Electrochemical Cell and Its Application as a Glucose Sensor", Sensors and Actuators, Jun. 1989, vol. 18, No. 1, pp. 59-70.
Gortan, L. et al., "Amperometric Glucose Sensors Based on Immobilized Glucose-Oxidizing Enymes and Chemically Modified Electrodes," Analytica Chimica Acta, 1991, vol. 249, No. 1, pp. 43-54.
Gorton, L. et al., "Amperometric Biosensors Based on an Apparent Direct Electron Transfer Between Electrodes and Immobilized Peroxiases," Analyst, Aug. 1992, vol. 117, pp. 1235-1241.
Gough, D. A. et al., "Two-Dimensional Enzyme Electrode Sensor for Glucose", Analytical Chemistry, 1985, vol. 57, No. 5, pp. 2351-2357.
Gregg, B. A. et al., "Redox Polymer Films Containing Enzymes. 1. A Redox-Conducting Epoxy Cement: Synthesis, Characterization, and Electrocatalytic Oxidation of Hydroquinone", The Journal of Physical Chemistry, 1991, vol. 95, No. 15, pp. 5970-5975.
Gregg, B.A. et al., "Cross-Linked Redox Gels Containing Glucose Oxidase for Amperometric Biosensor Applications", Analytical Chemistry, 1990, vol. 62, No. 3, pp. 258-263.
Harvey R, et al., "Design of the Glucose Rate Increase Detector: a Meal Detection Module for the Health Monitoring System", Journal of Diabetes Science and Technology, 2014, vol. 8(2), pp. 307-320.
Hashiguchi, Y. et al., "Development of a Miniaturized Glucose Monitoring System by Combining a Needle-Type Glucose Sensor With Microdialysis Sampling Method," Diabetes Care, May 1994, vol. 17, No. 5, pp. 387-396.
Heller, A. et al., "Electrical Wiring of Redox Enzymes", Accounts of Chemical Research, 1990, vol. 23, No. 5, pp. 128-134.
Hirsch, I. B. et al., "Intensive Insulin Therapy for Treatment of Type I Diabetes", Diabetes Care, Dec. 1990, vol. 13, No. 12, pp. 1265-1283.
International Preliminary Report on Patentability dated Mar. 8, 2018 in Application No. PCT/US2016/047875.
International Search Report and Written Opinion dated Oct. 28, 2016 in PCT Application No. PCT/US2016/047875.
International Search Report from International Application No. PCT/US2002/03299, dated Oct. 31, 2002.
Jobst, G. et al., "Thin-Film Microbiosensors for Glucose-Lactate Monitoring",Analytical Chemistry, Sep. 15, 1996, vol. 68, No. 18, pp. 3173-3179.
Johnson, K.W. et al., "In Vivo Evaluation of an Electroenzymatic Glucose Sensor Implanted in Subcutaneous Tissue", Biosensors & Bioelectronics, 1992, vol. 7, No. 10, pp. 709-714.
Jonsson, G. et al., "An Electromechanical Sensor for Hydrogen Peroxide Based on Peroxidase Adsorbed on a Spectrographic Graphite Electrode," Electroanalysis, Sep. 1989, vol. 1, No. 5, pp. 465-468.
Kanapieniene, J. J. et al., "Miniature Glucose Biosensor with Extended Linearity," Sensors and Actuators B: Chemical, Dec. 1992, vol. 10, No. 1, pp. 37-40.
Kawamori, R. et al., "Perfect Normalization of Excessive Glucagon Responses to Intraveneous Arginine in Human Diabetes Mellitus With the Artificial Beta-Cell", Diabetes, Sep. 1980, vol. 29, No. 9, pp. 762-765.
Kazuhiko, T. et al., "Specific Complexation with Mono- and Disaccharides that can be Detected by Circular Dichroism", J. Org. Chem., 1991, vol. 56, pp. 4089-4091.
Kimura, J. et al., "An Immobilized Enzyme Membrane Fabrication Method", Biosensors, 1988, vol. 4, No. 1, pp. 41-52.
Koudelka, M. et al., "In-vivo Behaviour of Hypodermically Implanted Microfabricated Glucose Sensors", Biosensors & Bioelectronics, 1991, vol. 6, No. 1, pp. 31-36.
Koudelka, M. et al., "Planar Amperometric Enzyme-Based Glucose Microelectrode", Sensors Actuators, Jun. 15, 1989, vol. 18, No. 2, pp. 157-165.

(56) References Cited

OTHER PUBLICATIONS

Mahmoudi Z., et al., "A Multistep Algorithm for Processing and Calibration of Microdialysis Continuous Glucose Monitoring Data," Diabetes Technology Therapeutics, 2013, vol. 15(10), pp. 825-835.

Mastrototaro, J.J. et al., "An Electroenzymatic Glucose Sensor Fabricated on a Flexible Substrate", Sensors and Actuators B: Chemical, Aug. 1991, vol. 5, No. 1-4, pp. 139-144.

Mastrototaro, J.J., et al., "An Electroenzymatic Sensor Capable of 72 Hour Continuous Monitoring of Subcutaneous Glucose", 14th Annual International Diabetes Federation Congress, Washington D.C., Jun. 1991, pp. 23-28.

McKean, B. D. et al., "A Telemetry-Instrumentation System for Chronically Implanted Glucose and Oxygen Sensors", IEEE Transactions on Biomedical Engineering, Jul. 1988, vol. 35, No. 7, pp. 526-532.

Monroe, D., "Novel Implantable: Glucose Sensors", ACL, Dec. 1989, pp. 8-16.

Morff, R.J., et al., "Microfabrication of Reproducible, Economical, Electroenzymatic Glucose Sensors", Annual International Conference of the IEEE Engineering in Medicine and Biology Society, 1990, vol. 12, No. 2, pp. 483-484.

Moussy, F. et al., "Performance of Subcutaneously Implanted Needle-Type Glucose Sensors Employing a Novel Trilayer Coating," Analytical Chemistry, Aug. 1, 1993, vol. 65, No. 15, pp. 2072-2077.

Nakamoto, S. et al., "A Lift-Off Method for Patterning Enzyme-Immobilized Membranes in Multi-Biosensors", Sensors and Actuators , Feb. 1988, vol. 13, No. 2, pp. 165-172.

Nishida, K. et al., "Clinical Applications of the Wearable Artificel Endocrine Pancreas with the Newly Designed Needle-Type Glucose Sensor," Elsevier Sciences B.V., 1994, pp. 353-358.

Nishida, K. et al., "Development of a Ferrocene-mediated Needle-type Glucose Sensor Covered With Newly Designed Biocompatible Membrane, 2-methacryloyloxyethylphosphorylcholine-co-n-butyl Methacrylate", Medical Progress Through Technology, 1995, vol. 21, No. 2, pp. 91-103.

Poitout, V. et al., "A Glucose Monitoring System for on Line Estimation in Man of Blood Glucose Concentration Using a Miniaturized Glucose Sensor Implanted in the Subcutaneous Tissue and a Wearable Control Unit", Diabetologia, Jul. 1993, vol. 36, No. 7, pp. 658-663.

Prosecution History from U.S. Appl. No. 15/240,711, dated Jan. 23, 2018 through Jun. 26, 2019, 59 pp.

Reach, G. et al., "A Method for Evaluating in vivo the Functional Characteristics of Glucose Sensors", Biosensors, 1986, vol. 2, No. 4, pp. 211-220.

|  | PATIENT 1 | PATIENT 2 |
|---|---|---|
| MODEL EQUATION | $\mu_{SG\_ROC\_TOTAL} + \mu_{\|SG\_ROC\_HALF1\|} + P_{MEAL} + (TS_{MEAL} * \Delta SG) + (\mu_{SG\_ROC\_HALF2} * \sigma_{SG\_ROC\_HALF2})$ | $\sigma_{SG\_ROC\_HALF1} + P\_MEAL$ |
| MODEL EQUATION | 364 | 5 |
| TOTAL CGM SAMPLES | 72,660 | 967 |
| TRAINING | | |
| MEAL COUNT | 813 | 5 |
| NONMEAL COUNT | 3,833 | 55 |
| TEST | | |
| MEAL COUNT | 215 | 5 |
| NONMEAL COUNT | 1103 | 15 |
| MODEL PERFORMANCE | | |
| ACCURACY | 96% | 88% |
| SENSITIVITY (TP) | 86% | 100% |
| SPECIFICITY (TN) | 98% | 87% |

FIG. 5

PERSONALIZED EVENT DETECTION

CROSS-REFERENCE TO RELATED APPLICATION(S)

This application is a continuation of U.S. patent application Ser. No. 17/652,816, filed Feb. 28, 2022 and titled "PERSONALIZED EVENT DETECTION," which is a continuation of U.S. patent application Ser. No. 16/579,651, filed Sep. 23, 2019 and titled "PERSONALIZED EVENT DETECTION METHODS AND RELATED DEVICES AND SYSTEMS," which is a continuation of U.S. patent application Ser. No. 15/240,711, filed Aug. 18, 2016 and titled "PERSONALIZED EVENT DETECTION METHODS AND RELATED DEVICES AND SYSTEMS," which claims the benefit of the following United States Provisional Patent Applications: U.S. Provisional Patent Application Ser. No. 62/208,479, filed Aug. 21, 2015 and titled "SENSOR CORE DATA SCIENCE"; U.S. Provisional Patent Application Ser. No. 62/266,820, filed Dec. 14, 2015 and titled "MEAL DETECTION MODEL AND IMPLEMENTATION FOR USE IN MOBILE APPLICATIONS AND PREDICTIVE ANALYTICS"; U.S. Provisional Patent Application Ser. No. 62/286,828, filed Jan. 25, 2016 and titled "GLYCEMIC INSIGHT ALGORITHMS AND IMPLEMENTATION FOR USE IN MOBILE APPLICATIONS AND PREDICTIVE ANALYTICS"; U.S. Provisional Patent Application Ser. No. 62/304,605, filed Mar. 7, 2016 and titled "GLYCEMIC INSIGHT ALGORITHMS AND IMPLEMENTATION FOR USE IN MOBILE APPLICATIONS AND PREDICTIVE ANALYTICS"; U.S. Provisional Patent Application Ser. No. 62/304,609, filed Mar. 7, 2016 and titled "INSIGHT GENERATION LOGIC BREAK DOWN (CURRENT LOGIC); U.S. Provisional Patent Application Ser. No. 62/304,615, filed Mar. 7, 2016 and titled "RETROSPECTIVE INSIGHT ALGORITHMS AND IMPLEMENTATION FOR DIABETES PATIENT ENGAGEMENT IN MOBILE APPLICATIONS"; U.S. Provisional Patent Application Ser. No. 62/304,618 filed Mar. 7, 2016 and titled "LIST OF ALL INSIGHTS"; and U.S. Provisional Patent Application Ser. No. 62/329,021, filed Apr. 28, 2016 and titled "'GLUCOSE ASSIST' SYSTEM." Each of these applications is incorporated by reference herein in its entirety and for all purposes.

TECHNICAL FIELD

Subject matter described herein relates generally to personalized event detection.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Control schemes have been developed that allow insulin infusion pumps to monitor and regulate a user's blood glucose level in a substantially continuous and autonomous manner. However, regulating blood glucose level is still complicated by variations in the response time for the type of insulin being used along with variations in a user's individual insulin response and daily activities (e.g., exercise, carbohydrate consumption, bolus administration, and the like). Additionally, manually-initiated deliveries of insulin prior to or contemporaneously with consuming a meal (e.g., a meal bolus or correction bolus) also influence the overall glucose regulation, along with various patient-specific ratios, factors, or other control parameters.

Continuous monitoring provides a greater understanding of the condition of a patient with diabetes. That said, there is also a burden imposed on patients, physicians and other healthcare providers to adapt to continuous monitoring and incorporate the amount of available data in a manner that allows for improved patient outcomes. While meals can be a major contributor to blood glucose variations, manual input is generally relied on to identify when meals occur and what the corresponding glucose response. However, many patients find manually indicating meals to be unnecessarily burdensome. In other instances, a patient may simply forget to provide a meal indication or be unable to provide a meal indication due to time or social constraints. Thus, for any given patient, a relatively large number of meals may occur without any indication that facilitates further analysis or monitoring. Accordingly, there is a need to identify meals and corresponding glucose responses without relying on manual interaction.

BRIEF SUMMARY

Disclose herein are techniques related to personalized event detection. The techniques may be practiced using a processor-implemented method; a system comprising one or more processors and one or more processor-readable storage media; and/or one or more non-transitory processor-readable storage media.

In some embodiments, the techniques may involve obtaining a plurality of glucose measurements indicative of a glucose level in a body of a patient during an analysis interval. The techniques may involve determining one or more glucose measurement statistics based on the plurality of glucose measurements. The techniques may involve determining a likelihood of the patient having consumed a meal during the analysis interval based on the one or more glucose measurement statistics that are correlative to an occurrence of a meal for the patient. The techniques may involve detecting an occurrence of the meal during the analysis interval based on the likelihood of the patient having consumed the meal during the analysis interval.

In some embodiments, the techniques may involve obtaining a plurality of glucose measurements indicative of a glucose level in a body of a patient during an analysis interval. The techniques may involve determining one or more glucose measurement statistics based on the plurality of glucose measurements. The techniques may involve determining a likelihood of the patient having consumed a meal during the analysis interval using a patient-specific meal detection model and the one or more glucose measurement statistics. The techniques may involve detecting an occurrence of the meal during the analysis interval based on the likelihood of the patient having consumed the meal during the analysis interval.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

FIG. 5 is a table depicting an exemplary meal detection models generated for different patients in conjunction with the patient modeling process of FIG. 2 in one or more exemplary embodiments;

DETAILED DESCRIPTION

Figure 1:
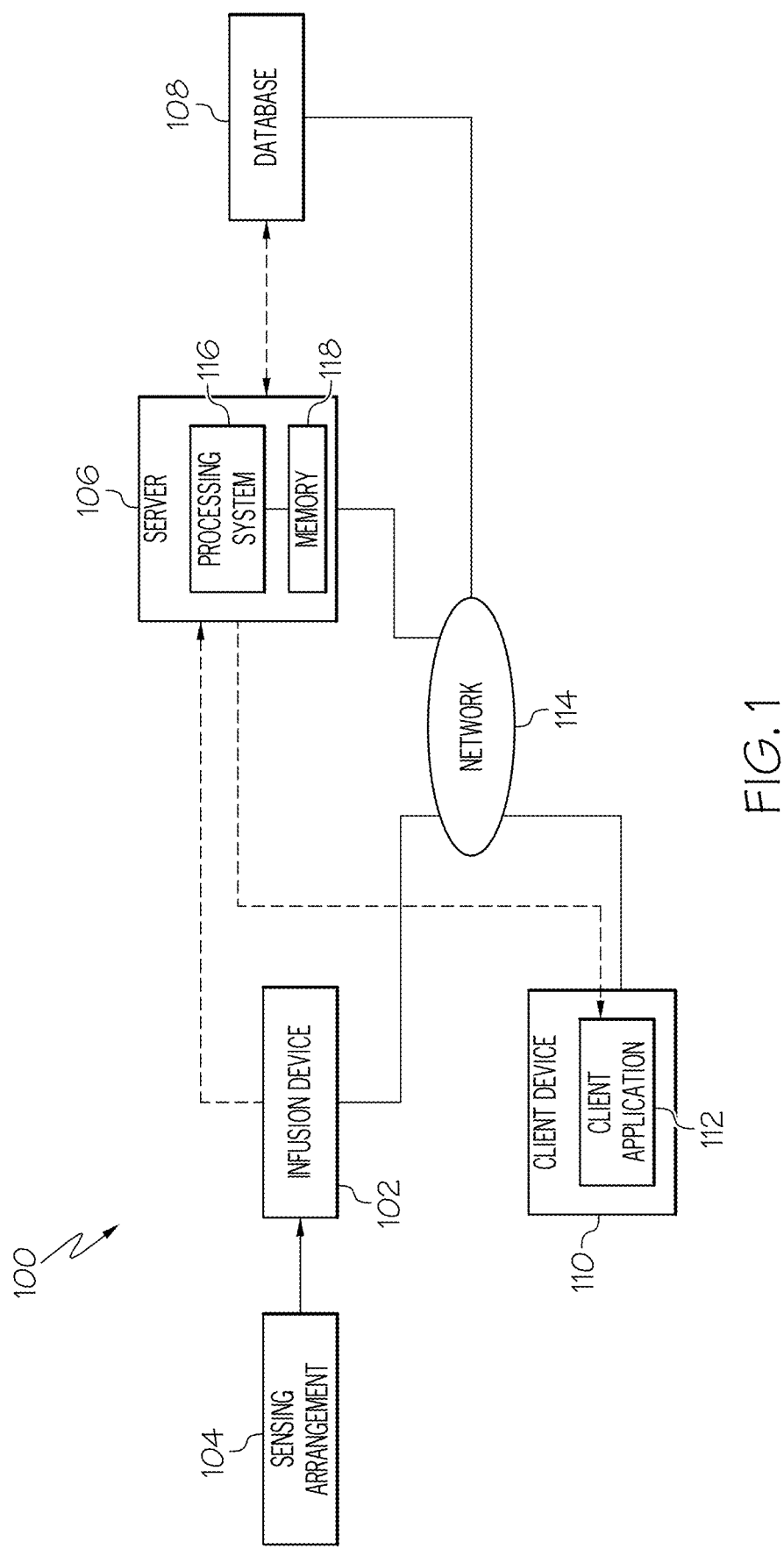
FIG. 1 depicts an exemplary embodiment of a patient management system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Exemplary embodiments of the subject matter described herein are implemented in conjunction with medical devices, such as portable electronic medical devices. Although many different applications are possible, the following description focuses on embodiments that incorporate a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference. That said, the subject matter described herein can be utilized more generally in the context of overall diabetes management or other physiological conditions independent of or without the use of an infusion device or other medical device (e.g., when oral medication is utilized), and the subject matter described herein is not limited to any particular type of medication.

Generally, a fluid infusion device includes a motor or other actuation arrangement that is operable to linearly displace a plunger (or stopper) of a reservoir provided within the fluid infusion device to deliver a dosage of fluid, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

Exemplary embodiments described herein generally relate to systems for analyzing and presenting information pertaining to operation of an infusion device delivering fluid to a body of a user, and in particular, information pertaining to events occurring during operation. For example, in one or more embodiments, a snapshot graphical user interface (GUI) display may be presented that includes graphical indicia of event pattern(s) identified during preceding operation of the infusion device. The event pattern information may be utilized by the patient, the patient's doctor or other health care provider, or another individual to assess the efficacy of the regulation achieved by the infusion device, identify potential causes of an event pattern, and identify potential actions that may improve the quality of control achieved by the infusion device.

In exemplary embodiments described herein, events occurring during operation of an infusion device are capable of being detected autonomously and without reliance on any manual interaction or inputs using a personalized, patient-specific event detection model. The event detection model relies on input variables that have been identified as predictive or correlative to an occurrence of the event for that patient, which may include patient-specific event probabilities determined based on historical event data associated with the patient and one or more measurement statistics determined based on measurement data for a physiological condition of the patient. In this regard, for each patient, the particular subset of measurement statistics that are predictive or correlative to the event for that patient may be different from those of other patients, and similarly, whether the historical event probability is predictive or correlative to the event may also vary on a patient-by-patient basis. Additionally, the patient-specific event detection model also utilizes correlation coefficient values to weight the relative predictiveness or correlative strength of each model input variable. Thus, the model determines a metric indicative of the likelihood of an occurrence or an absence of the event based on the patient-specific predictive subset of measurement statistics and corresponding patient-specific correlation coefficient values. In some embodiments, events may be identified substantially in real-time.

In exemplary embodiments, the events to be detected are meals occurring during monitoring of a patient's glucose levels and corresponding operation of an insulin infusion device. In this regard, a patient-specific meal detection model is employed to calculate or otherwise determine a metric indicative of whether or not a meal corresponding to a current analysis interval has occurred based on a subset of glucose measurement statistics that have been identified as predictive of or correlative to consumption of a meal by the patient based on the patient's historical meal and bolus information. For some patients, the meal detection model may also incorporate a meal probability metric for the current analysis interval that reflects the likelihood of the patient consuming a meal contemporaneously or concurrently to the current analysis interval based on the patient's historical meal distribution. Values for the predictive subset of glucose measurement statistics are calculated based on glucose measurement data corresponding to the current analysis interval and a meal probability metric for the current analysis interval is also determined, and the respective correlation coefficients from the meal detection model are applied to the current values for the predictive subset of glucose measurement statistics and the current meal probability to obtain a meal consumption metric value. The meal consumption metric value is then utilized to determine whether a meal has been consumed during the current analysis interval.

When consumption of a meal is detected, the glucose measurement data associated with the current analysis interval may be flagged, marked, or otherwise stored in association with an identifier that indicates a meal associated with the analysis interval corresponding to that subset of the glucose measurement data. Accordingly, any notifications, alerts, displays, or other actions that would otherwise be undertaken in response to a manually-indicated or announced meal may be similarly performed in response to or in a manner that is influenced by a meal detected by the meal detection model. Thus, meals may be autonomously identified and automatically reflected by subsequent operation of the infusion device or displays pertaining thereto without requiring any manual interaction. Not only is the patient alleviated of the burdens associated with manually announcing meals, but inadvertently omitted meal indications may also be accounted for. As a result, the number of meals for which data may be captured and analyzed may increase, which, in turn, may increase the accuracy or reliability of meal response-related analysis, and thereby improve patient outcomes.

FIG. 1 depicts an exemplary embodiment of a patient management system 100. The patient management system 100 includes an infusion device 102 that is communicatively coupled to a sensing arrangement 104 to obtain measurement data indicative of a physiological condition in the body of a patient, such as sensor glucose measurement values, as described in greater detail below in the context of FIGS. 9-12. In exemplary embodiments, the infusion device 102 operates autonomously to regulate the patient's glucose level based on the sensor glucose measurement values received from the sensing arrangement 104 as described in greater detail below in the context of FIGS. 13-15.

In the illustrated embodiment, the infusion device 102 periodically uploads or otherwise transmits the measurement data (e.g., sensor glucose measurement values and timestamps associated therewith) to a remote device 106 via a communications network 114, such as a wired and/or wireless computer network, a cellular network, a mobile broadband network, a radio network, or the like. That said, in other embodiments, the sensing arrangement 104 may be communicatively coupled to the communications network 114 to periodically upload or otherwise transmit measurement data to the remote device 106 via the communications network 114 independent of the infusion device 102. Additionally, in some embodiments, the infusion device 102 also uploads delivery data and/or other information indicative of the amount of fluid delivered by the infusion device and the timing of fluid delivery, which may include, for example, information pertaining to the amount and timing of manually-initiated boluses and associated meal announcements. Some examples of an infusion device uploading measurement and delivery data to a remote device are described in United States Patent Application Publication Nos. 2015/0057807 and 2015/0057634, which are incorporated by reference herein in their entirety.

The remote device 106 is coupled to a database 108 configured to store or otherwise maintain the historical measurement and delivery data received from the infusion device 102 in association with a patient associated with the infusion device 102 (e.g., using unique patient identification information). Additionally, the database 108 may store or otherwise maintain, in association with a particular patient, a personalized and patient-specific event detection model. In this regard, the event detection model defines which input variables or parameters are to be factored in when making a determination of whether or not an event has occurred along with relative weightings assigned to those inputs corresponding to how predictive or correlative the value of a respective model input value is to the occurrence of the event to be detected, as described in greater detail below in the context of FIGS. 2-6. The remote device 106 generally represents an electronic device configured to analyze or otherwise monitor the measurement and delivery data obtained for the patient associated with the infusion device 102, generate patient-specific event detection models based on a respective patient's historical measurement and delivery data, and generate or otherwise facilitate a GUI display that is influenced by or otherwise reflects the detected events. The GUI display may be presented on the remote device 106 or another electronic device 110, alternatively referred to herein as a client device. In practice, the remote device 106 may reside at a location that is physically distinct and/or separate from the infusion device 102, such as, for example, at a facility that is owned and/or operated by or otherwise affiliated with a manufacturer of the infusion device 102. For purposes of explanation, but without limitation, the remote device 106 may alternatively be referred to herein as a server.

The remote device 106 generally represents a computing system or another combination of processing logic, circuitry, hardware, and/or other components configured to support the processes, tasks, operations, and/or functions described herein. In this regard, the server 106 includes a processing system 116, which may be implemented using any suitable processing system and/or device, such as, for example, one or more processors, central processing units (CPUs), controllers, microprocessors, microcontrollers, processing cores and/or other hardware computing resources configured to support the operation of the processing system 116 described herein. The processing system 116 may include or otherwise access a data storage element 118 (or memory) capable of storing programming instructions for execution by the processing system 116, that, when read and executed, cause processing system 116 to perform or otherwise support the processes, tasks, operations, and/or functions described herein. For example, in one embodiment, the instructions cause the processing system 116 to create, generate, or otherwise facilitate an application platform that supports instances of an application using data that is stored or otherwise maintained by the database 108. Depending on the embodiment, the memory 118 may be realized as a random access memory (RAM), read only memory (ROM), flash memory, magnetic or optical mass storage, or any other suitable non-transitory short or long term data storage or other computer-readable media, and/or any suitable combination thereof.

The client device 110 generally represents an electronic device coupled to the network 114 that may be utilized by a user to access and view data stored in the database 108 via the server 106. In practice, the client device 110 can be realized as any sort of personal computer, mobile telephone, tablet or other network-enabled electronic device that includes a display device, such as a monitor, screen, or another conventional electronic display, capable of graphically presenting data and/or information provided by the server 106 along with a user input device, such as a keyboard, a mouse, a touchscreen, or the like, capable of receiving input data and/or other information from the user of the client device 110. A user, such as the patient's doctor or another healthcare provider, manipulates the client device 110 to execute a client application 112 that contacts the server 106 via the network 114 using a networking protocol, such as the hypertext transport protocol (HTTP) or the like.

In exemplary embodiments described herein, a user of the client device 110 manipulates a user input device associated with the client device 110 to input or otherwise provide indication of the patient associated with the infusion device 102 along with a period of time for which the user would like to review, analyze, or otherwise assess measurement data associated with the patient. In response, the server 106 accesses the database 108 to retrieve or otherwise obtain historical measurement data associated with the identified patient for the identified time period and generates a GUI display that is presented on the display device associated with the client device 110 via the client application 112 executing thereon.

It should be appreciated that FIG. 1 depicts a simplified representation of a patient management system 100 for purposes of explanation and is not intended to limit the subject matter described herein in any way. For example, in various embodiments, a GUI display may be presented on any device within the patient management system 100 (e.g., the server 106, the infusion device 102, the sensing arrangement 104, or the like) and not necessarily on the client device 110. Moreover, in some embodiments, the infusion device 102 may be configured to store or otherwise maintain historical measurement and delivery data onboard the infusion device 102 and generate GUI displays on a display device associated with the infusion device 102, in which case one or more of the server 106, the database 108, and the client device 110 may not be present. Additionally, the subject matter described herein is not limited to meal detection or event detection for purposes of generating GUI displays, and in various embodiments, meal or event detection may be utilized to dynamically adjust operation or otherwise influence the control scheme of the infusion device 102 (e.g., by adjusting one or more thresholds or parameters influencing delivery, notifications, alerting, or the like), generate alerts or other user notifications, or perform other actions in response to the detected meal or event.

Figure 2:
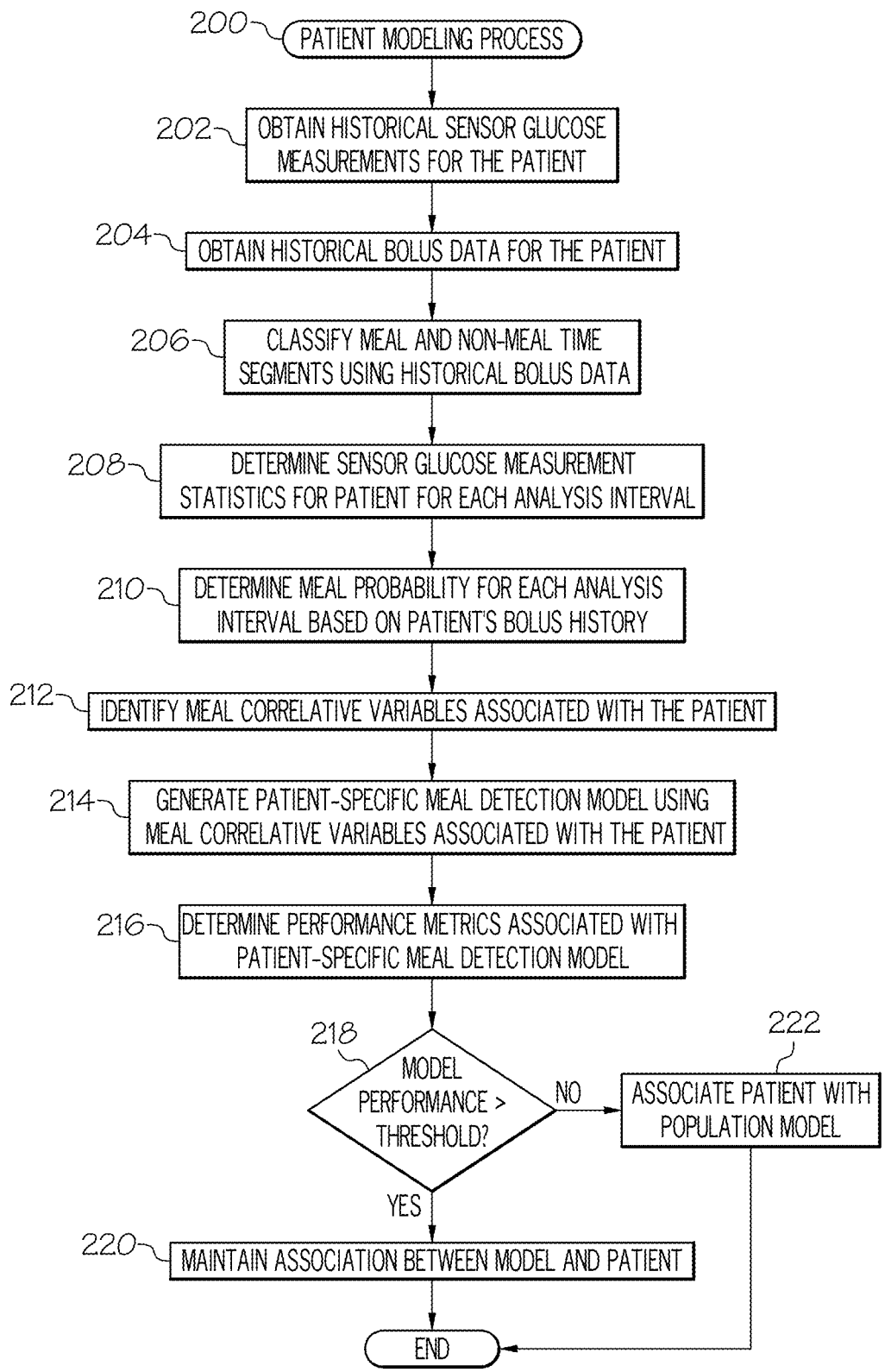
FIG. 2 is a flow diagram of an exemplary patient modeling process suitable for use with the patient management system of FIG. 1 in one or more exemplary embodiments.

FIG. 2 depicts an exemplary patient modeling process 200 suitable for implementation by a patient management system to develop a patient-specific event detection model. The various tasks performed in connection with the patient modeling process 200 may be performed by hardware, firmware, software executed by processing circuitry, or any combination thereof. For illustrative purposes, the following description refers to elements mentioned above in connection with FIG. 1. In practice, portions of the patient modeling process 200 may be performed by different elements of the patient management system 100, such as, for example, the infusion device 102, the sensing arrangement 104, the server 106, the database 108, the client device 110, the client application 112, and/or the processing system 116. It should be appreciated that the patient modeling process 200 may include any number of additional or alternative tasks, the tasks need not be performed in the illustrated order and/or the tasks may be performed concurrently, and/or the patient modeling process 200 may be incorporated into a more comprehensive procedure or process having additional functionality not described in detail herein. Moreover, one or more of the tasks shown and described in the context of FIG. 2 could be omitted from a practical embodiment of the patient modeling process 200 as long as the intended overall functionality remains intact.

The patient modeling process 200 begins by obtaining historical measurement data for the patient of interest and obtaining historical bolus data for the patient over the period corresponding to the historical measurement data (tasks 202, 204). In this regard, the patient modeling process 200 may be initiated or performed after the server 106 has acquired and stored sufficient sensor glucose measurement values and bolus information in the database 108. For example, the infusion device 102 may periodically upload, to the server 106 via the network 114, reference blood glucose measurement values obtained from the body of the patient (e.g., using a blood glucose meter or fingerstick device) along with bolus information including the timings and amounts of insulin delivered, including indications of whether a particular bolus is a meal bolus or otherwise associated with a meal. The bolus information may also include the amount of carbohydrates consumed, the type of meal, or the like. In this regard, in the absence of an explicit meal indication or announcement from the patient, the server 106 may automatically classify a bolus delivered as a meal bolus when a carbohydrate entry occurred within a threshold amount of time of the bolus being delivered (e.g., within 5 minutes). Additionally, the infusion device 102 (or alternatively, the sensing arrangement 104) may periodically upload, to the server 106, sensor glucose measurement values obtained from the body of the patient by the sensing arrangement 104.

In one or more embodiments, the server 106 stores or otherwise maintains, in the database 108, one or more files or entries associated with the patient that maintains an association between the patient's historical sensor glucose measurement data, the patient's historical bolus and meal data, the patient's historical reference blood glucose measurements, and the like. Once a sufficient amount of data has been obtained by the server 106 and/or the database 108, the patient modeling process 200 continues with determining a patient-specific meal detection model based on the patient's historical sensor glucose measurement and bolus data. In one embodiment, the patient modeling process 200 requires that data for at least a minimum threshold number of days (or hours) has been uploaded to continue. In other embodiments, additional thresholds may be utilized to determine when modeling can occur, such as, for example, a minimum average number of meal boluses per day of data, a minimum average number of reference blood glucose values per day of data, or the like.

In some embodiments, the server 106 also performs or otherwise implements one or more data cleaning or data preparation processes on the data to reduce noise or transients within the data, such as, for example, low-pass filtering the sensor glucose measurement values or otherwise filtering, excluding, or mitigating the impact of portions of data accompanied by variables that could cause variations that would reduce accuracy or reliability of the model. For example, the server 106 may identify and reduce or otherwise eliminate the impact of data associated with periods of time involving anomalous measurement data, such as, for example, artifacts, dropouts, or the like. In some embodiments, the measurement data associated with or potentially influenced by artifacts, dropouts or other anomalous sensor behavior may be detected by either the sensing arrangement 104 or the infusion device 102 instead of the server 106. Examples of artifact or dropout detection are described in U.S. Patent Application Pub. No. 2015/0328402 and incorporated by reference herein. In other embodiments, the data cleaning or filtering may also account for suspension of delivery by the infusion device 102 or meals accompanied by stacked boluses, anomalous or unusual carbohydrate amounts, anomalous or unusual bolus dosages, particular bolus types, anomalous or unusual carbohydrate ratios, anomalous or unusual sensitivity factors, anomalous or unusual glucose targets, anomalous or unusual basal rates, anomalous or unusual active insulin amounts, or the like.

Once sufficient historical measurement and bolus data is obtained, the patient modeling process 200 continues by classifying or categorizing segments of time within the period of time encompassed by the historical data into meal or non-meal time segments (task 206). In an exemplary embodiment, a meal segment is defined as a one hour segment of historical sensor glucose measurement values that starts around the time of a meal bolus (at, before or after) and precedes the highest or maximum sensor glucose measurement value within the 90 minutes following the meal bolus, where that meal bolus is also associated with a carbohydrate amount greater than a minimum threshold (e.g., 0 grams), is delivered within a maximum amount of time difference (e.g., 5 minutes) before or after the carbohydrate entry, and is not preceded by another meal bolus within 3 hours of the reference meal bolus associated with the meal segment. In this regard, the threshold criteria are intended to diminish the effects of active insulin from other boluses and ensure the meal segments reliably reflect a characteristic meal response of the patient. In exemplary embodiments, a non-meal segment is defined as a one hour segment of historical sensor glucose measurement values that precedes or follows a meal segment. Historical sensor glucose measurement values that are not classified into a meal or non-meal segment are not utilized for purposes of generating the model due to those segments of data potentially exhibiting responses to residual active insulin from preceding meal boluses, as well as maintaining segments of consistent duration. In one or more embodiments where an absolute timestamp is available for when a patient begins eating a meal (e.g., by a user indication via the client application 112), a meal segment may be defined as the one hour segment of historical sensor glucose measurement values that starts at that time.

Figure 3:
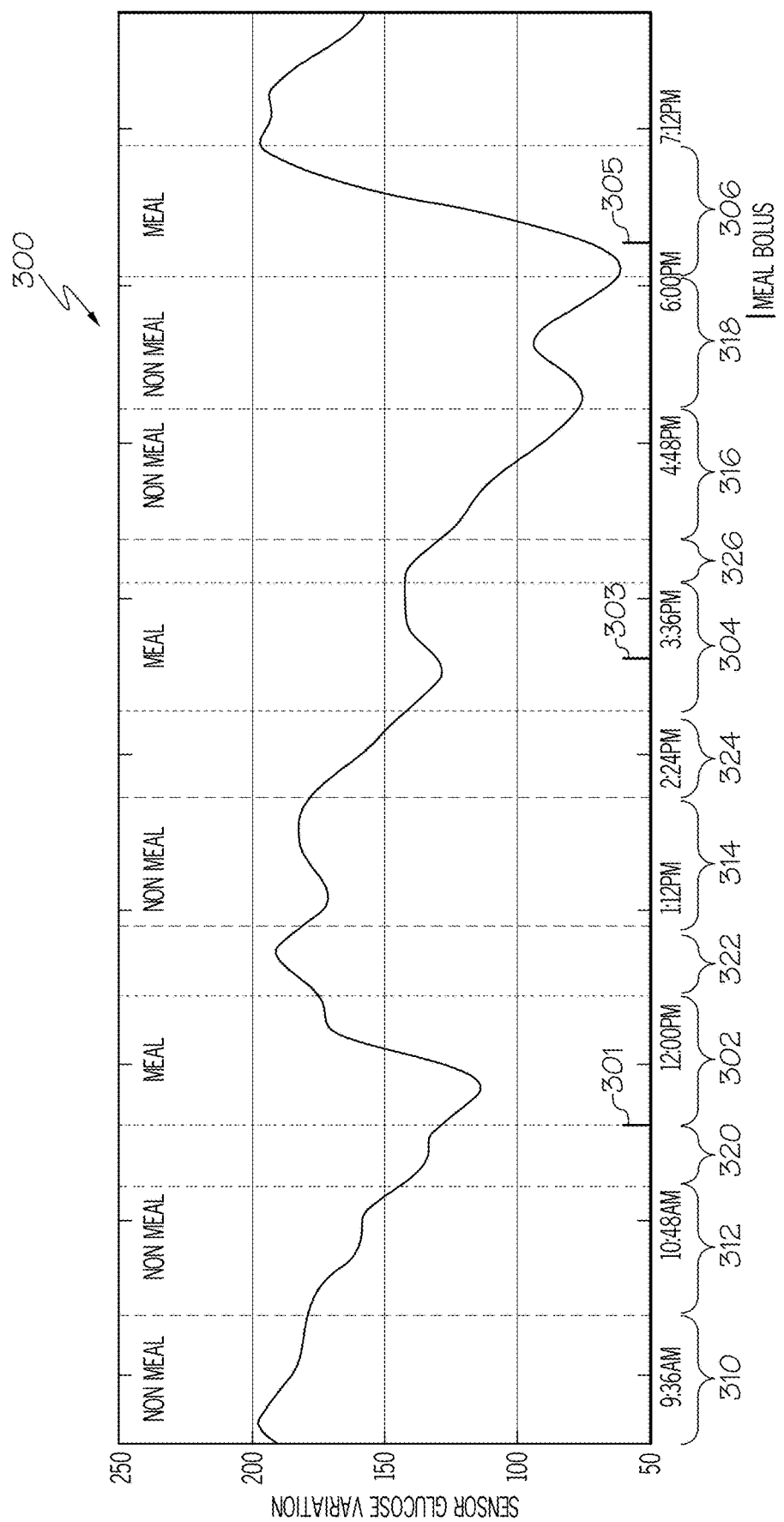
FIG. 3 is a graph depicting an exemplary relationship of sensor glucose measurement values with respect to time in accordance with one embodiment suitable for use with the patient modeling process of FIG. 2 in one or more exemplary embodiments.

FIG. 3 depicts an exemplary graph 300 of sensor glucose measurement values with respect to time illustrating one example of how sensor glucose measurement data could be classified into different meal or non-meal segments based on meal bolus indications and the sensor glucose measurement values. In the illustrated example, segments 302, 304, 306 of sensor glucose measurement values around meal bolus indications 301, 303, 305 are classified as meal segments, with segments 310, 312, 314, 316 and 318 preceding the respective meal segments 302, 304, 306 being classified as non-meal segments. Here, it is noted that intervening segments 320, 322, 324, 326 between meal segments 302, 304 and non-meal segments 312, 314, 316 do not satisfy the criteria for being classified as either a meal or non-meal segment, and therefore, are excluded from further use in developing a meal detection model.

Referring again to FIG. 2, after classifying the historical sensor glucose measurement data for the patient into meal and non-meal segments, the patient modeling process 200 continues by calculating or otherwise determining sensor glucose measurement statistics associated with the respective segments based on the sensor glucose measurement values corresponding to that respective segment (task 208). In this regard, the sensor glucose measurement statistics characterize the patient's glucose level within or during the respective segment. For example, in one embodiment, for each one hour meal or non-meal segment, the server 106 calculates a mean or average sensor glucose measurement value over that one hour period, a standard deviation of the sensor glucose measurement values during that one hour period, a mean or average rate of change of the sensor glucose measurement values on a sample-to-sample basis during that one hour period, mean or average rate of changes of the sensor glucose measurement values on a sample-to-sample basis for discrete time periods within that one hour period (e.g., within the first 30 minutes and the second 30 minutes), standard deviations associated with those rate of change values, an absolute amplitude of the sensor glucose measurement values during that segment (e.g., the difference between the maximum and minimum values within that segment), and an amplitude difference between the first and last glucose measurement value of that segment (e.g., by subtracting the first glucose measurement value from the last glucose measurement value).

Figure 4:
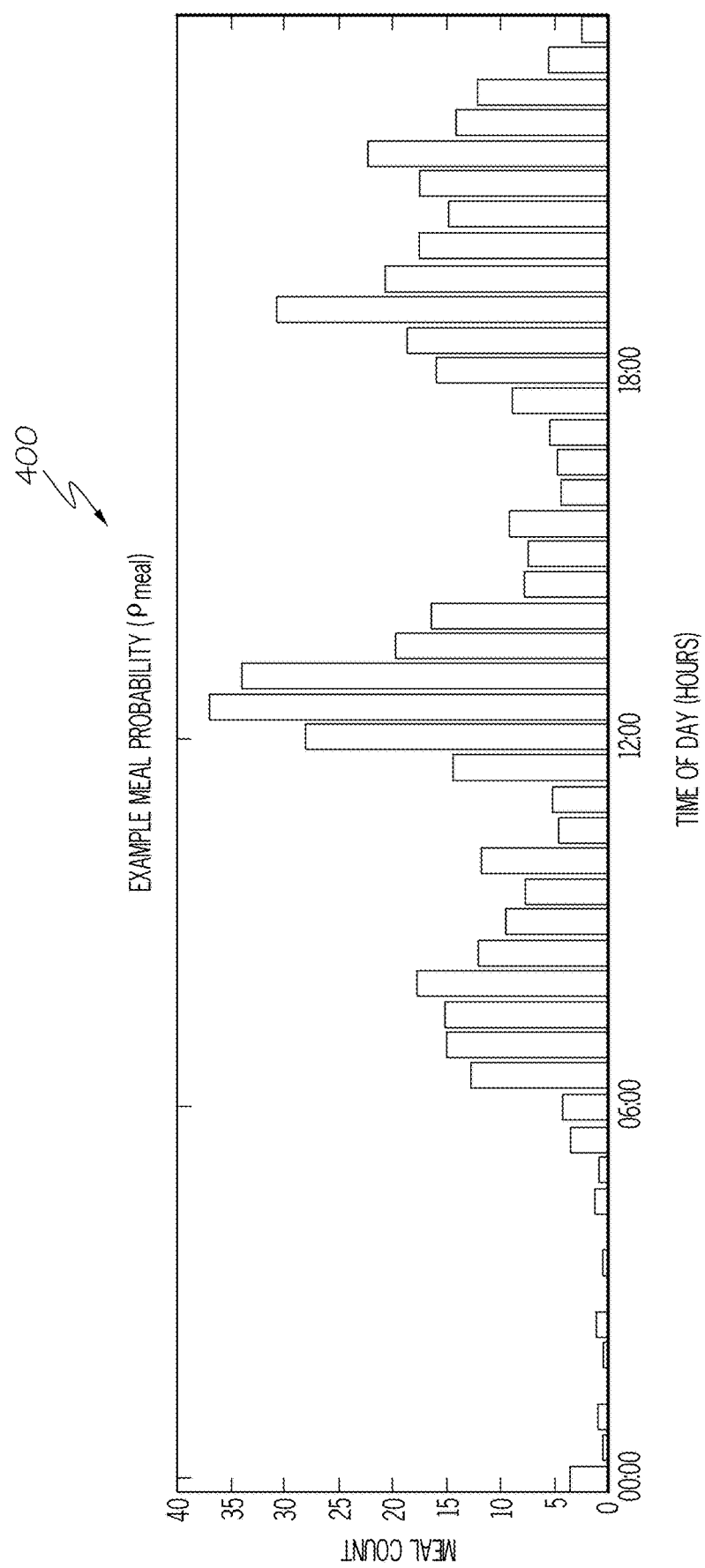
FIG. 4 is a graph depicting an exemplary relationship of patient meal probability with respect to time in accordance with one embodiment suitable for use with the patient modeling process of FIG. 2 in one or more exemplary embodiments.

The patient modeling process 200 also calculates or otherwise determines a meal probability associated with the respective segments based on the patient's bolus history (task 210). In this regard, the server 106 analyzes the meal bolus indications associated with the patient to determine a meal probability distribution for the patient that represents the relative probability of the patient consuming a meal at a particular time of day. In one embodiment, the server 106 divides the period of a day into a plurality of intervals, with a respective meal probability associated with each interval being determined based on the number of meal bolus indications having an associated timestamp within that interval relative. For example, FIG. 4 depicts an exemplary meal distribution 400 with respect to the time of day divided into 30 minute intervals, resulting in 48 different intervals over a 24-hour period. The corresponding meal probability for each interval may be determined by dividing the number of meal boluses classified or assigned to that respective interval by the total number of meal boluses. Thereafter, each meal or non-meal segment may be assigned a corresponding meal probability value based on the corresponding intervals overlapped or concurrent to a respective segment.

In one embodiment, meal bolus instances for a patient are grouped into 10 minute intervals, resulting in 144 different intervals over a 24-hour period. For example, for a meal segment 302 spanning from 11:30 AM to 12:30 PM, the server 106 may determine a meal probability associated with that meal segment 302 as a sum of the number of instances of meal boluses with the six ten minute intervals encompassed by the meal segment (e.g., the 11:30 AM-11:40 AM interval, the 11:40 AM-11:50 AM interval, the 11:50 AM-12:00 PM interval, and so on) and then dividing the resultant sum by the total number of instances of meal boluses in the patient's history. It should be noted that 10 minute intervals are depicted and described for purposes of explanation, but in practice, the meal probability intervals are not limited to any particular length or duration, and may be shorter or longer than 10 minutes to achieve a desired level of granularity.

Still referring to FIG. 2, after determining the sensor glucose measurement statistics and meal probability values associated with each respective meal segment or non-meal segment, the patient modeling process 200 continues by identifying a subset of the sensor glucose measurement statistics and meal probability values that are predictive or correlative to the occurrence of a meal for that individual patient and generating a patient-specific meal detection model for that patient using that predictive subset of variables (tasks 212, 214). In this regard, in exemplary embodiments, the server 106 utilizes machine learning to determine which of the sensor glucose measurement statistics and the meal probability value are most strongly correlated to or predictive of each segment being of the classified type, and then determines a corresponding equation for calculating a metric indicative of whether or not a segment is a meal segment based on that subset of variables. Thus, the model is capable of characterizing or mapping the patient's response evidenced by the sensor glucose measurement values to that of a meal, and vice versa. Since each patient's response may vary from the rest of the population, the subset of sensor glucose measurement statistics that are predictive of or correlative to a meal for that patient may vary from other users. Additionally, the relative weightings applied to the respective statistics of that predictive subset may also vary from other patient's who may have common predictive subsets, based on differing correlations between a particular glucose measurement statistic and the meal response of that particular patient.

In one embodiment, stepwise logistic regression is utilized by the server 106 to determine what sensor glucose measurement statistics among the plurality of sensor glucose measurement statistics determined at task 208 are predictive of a meal for the patient of interest, as well as identifying whether the meal probability values determined at task 210 for that patient are predictive. In this regard, the meal probability value may not be predictive or correlative for a patient that grazes or consumes meals throughout the day, while the meal probability value may be highly predictive or correlative for a patient that grazes or consumes meals at relatively defined times of day. In some embodiments, the relative strength of correlation for each of those predictive variables may be utilized to determining a weighting or scaling for the values of those variables to arrive at an output from the model (e.g., by applying those weightings to those variable values) that indicates the occurrence or non-occurrence of a meal during an analysis interval (e.g., a one hour segment of sensor glucose measurement values). In other embodiments, multiple predictive variables may be multiplied or otherwise factored in with one another when values for those variables, in combination, are predictive or correlative to a meal.

In one or more exemplary embodiments, only a subset of the meal and non-meal segments for the patient are used to develop the meal detection model, with the remaining the meal and non-meal segments being utilized by the patient modeling process 200 to test or otherwise validate the developed model (tasks 216, 218). For example, for segments classified into the testing group of segments, the server 106 applies the developed meal detection model to the predictive variable values associated with the respective test segment, and then identifies or otherwise determines whether the model results in that test segment being classified as a meal segment or non-meal segment. Thereafter, the server 106 compares the model classification of each test segment to the previous classification (e.g., task 206) and calculates or otherwise determines one or more metrics indicative of the performance of the model with respect to the test segments. For example, the server 106 may determine an accuracy metric associated with the model based on the number of times the model correctly classified a test segment as a meal or non-meal segment. The server 106 may also calculate a sensitivity metric associated with the model as the ratio of the correctly detected number of meals by the model relative to the total number of meal segments in the test group. The server 106 may also calculate a specificity metric associated with the model as the ratio of the correctly detected number of non-meal segments by the model relative to the total number of non-meal segments in the test group.

When the performance metrics associated with the developed model are greater than or otherwise satisfy applicable validation criteria, the patient modeling process 200 stores or otherwise maintains the model in association with the patient for use in subsequently detecting meals that are not manually indicated or announced by the patient (task 220). For example, identification of the predictive variables for the patient along with the relative weightings or manner in which those predictive variables should be combined to obtain a metric indicative of a meal may be stored or otherwise maintained in the database 108 in association with a patient identifier assigned to or otherwise associated with the patient and/or the infusion device 102. Conversely, when the performance metrics associated with the developed model do not satisfy applicable validation criteria, the patient modeling process 200 discards the developed model and assigns or otherwise associates the patient with a broader population model (task 222). In this regard, the population model may be developed by performing various aspects of the patient modeling process 200 across meal and non-meal segments associated with a plurality of different patients. For example, in one embodiment, a patient may be assigned or otherwise associated with a particular group of patients having one or more characteristics in common, with a meal detection model for that patient group being determined based on meal and non-meal segments for the different patients of the group. In one or more embodiments, the patient modeling process 200 assigns or otherwise associates the patient with a patient group meal detection model upon initialization of the patient within the patient management system 100 prior to accumulating sufficient historical data for developing a patient-specific model.

FIG. 5 depicts a table 500 illustrating different meal detection models generated for different patients. A first patient (Patient 1) has 364 days worth of historical measurement and bolus data stored in the database 108 that includes 72,660 instances of sensor glucose measurement values that can be classified into 1028 meal segments and 4936 non-meal segments, which are further divided into a training group of segments (consisting of 813 meal segments and 3833 non-meal segments) and a test group of segments (consisting of 215 meal segments and 1103 non-meal segments). The server 106 analyzes the test group of segments and determines a patient-specific meal detection model 502 for Patient 1 that generates a metric indicative of a meal occurrence based on the predictive variables (or model inputs) of: mean sensor glucose rate of change over the preceding one hour of sensor glucose measurement values, mean sensor glucose rate of change over the first half hour of the preceding one hour of sensor glucose measurement values, the meal probability value associated with the preceding one hour interval, the product of the timestamp associated with the meal and the amplitude difference of the sensor glucose measurement value over the preceding one hour interval, and the product of the mean and standard deviation of the sensor glucose rate of change over the second half hour of the preceding one hour of sensor glucose measurement values. After determining the model 502, the server 106 applies the model 502 to the testing group of segments and then determines performance metrics associated with the meal/non-meal outputs model 502. When the performance metrics satisfy validation criteria, the server 106 stores or otherwise maintains information defining the model 502 in the database 108 in association with Patient 1.

A second patient (Patient 2) has 5 days worth of historical measurement and bolus data stored in the database 108 that includes 967 instances of sensor glucose measurement values that can be classified into 10 meal segments and 70 non-meal segments, which are further divided into a training group of segments (consisting of 5 meal segments and 55 non-meal segments) and a test group of segments (consisting of 5 meal segments and 15 non-meal segments). The server 106 analyzes the test group of segments and determines a patient-specific meal detection model 504 for Patient 2 that generates a metric indicative of a meal occurrence based on the predictive variables (or model inputs) of: standard deviation of the sensor glucose rate of change over the first half hour of the preceding one hour of sensor glucose measurement values and the meal probability value associated with the one hour interval. After determining the model 504, the server 106 applies the model 504 to the testing group of segments and then determines performance metrics associated with the meal/non-meal outputs of the model 504. In this regard, if the performance metrics satisfy validation criteria, the server 106 discards the model 504 or otherwise fails to store the model 504 in association with Patient 2. For example, if the validation criteria are an accuracy greater than 95%, a sensitivity greater than 80%, and a specificity greater than 80%, the Patient 1 model 502 may be validated and stored in association with Patient 1 while the Patient 2 model 504 fails the validation and is discarded or otherwise ignored in favor of a more generic population model for Patient 2.

Figure 6:
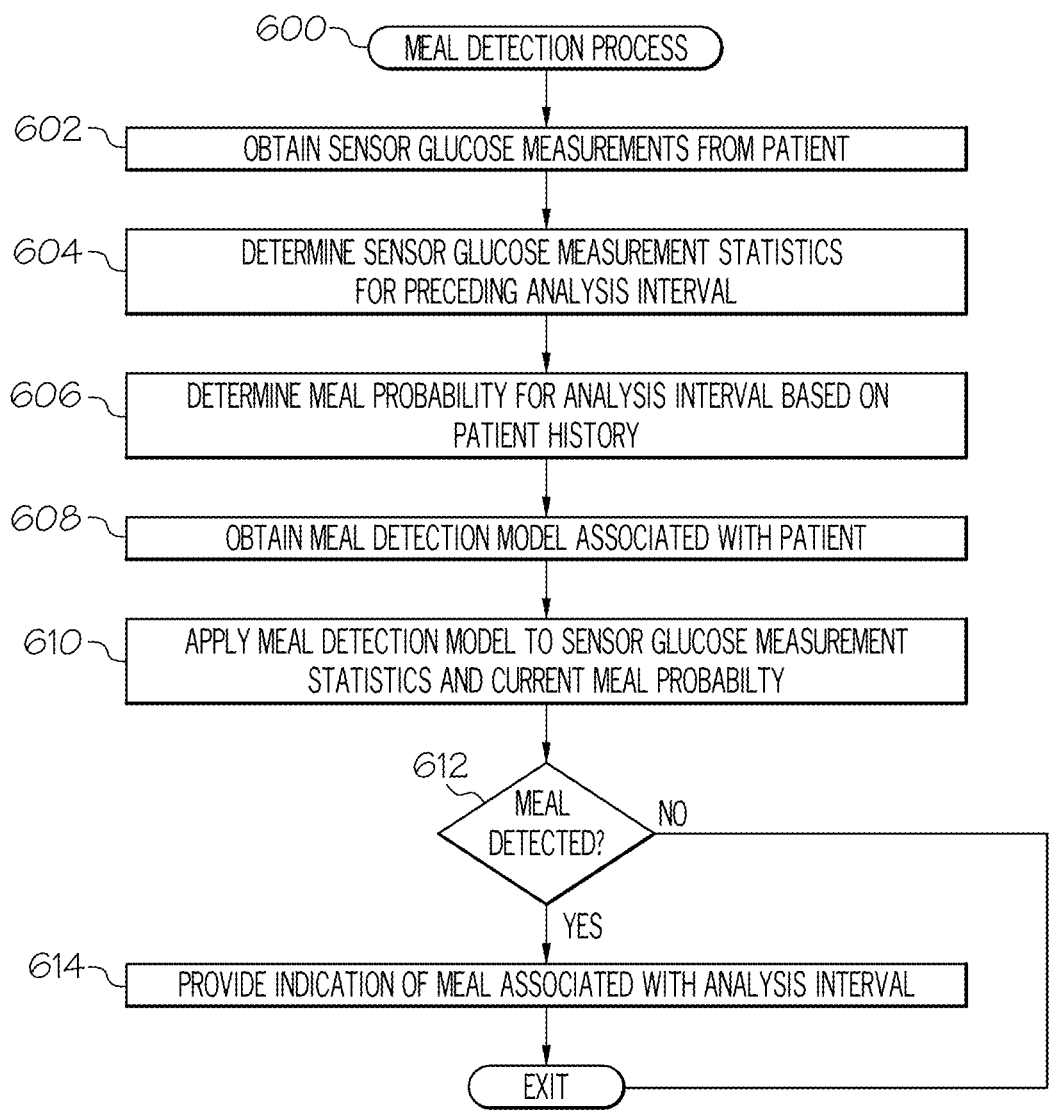
FIG. 6 is a flow diagram of an exemplary meal detection process suitable for use with a meal detection model generated by the patient modeling process of FIG. 2 in the patient management system of FIG. 1 in one or more exemplary embodiments.

FIG. 6 depicts an exemplary meal detection process 600 suitable for implementation by a patient management system to detect or otherwise identify unannounced meals using a patient-specific meal detection model. The various tasks performed in connection with the meal detection process 600 may be performed by hardware, firmware, software executed by processing circuitry, or any combination thereof. For illustrative purposes, the following description refers to elements mentioned above in connection with FIG. 1. In practice, portions of the meal detection process 600 may be performed by different elements of the patient management system 100, such as, for example, the infusion device 102, the sensing arrangement 104, the server 106, the database 108, the client device 110, the client application 112, and/or the processing system 116. It should be appreciated that the meal detection process 600 may include any number of additional or alternative tasks, the tasks need not be performed in the illustrated order and/or the tasks may be performed concurrently, and/or the meal detection process 600 may be incorporated into a more comprehensive procedure or process having additional functionality not described in detail herein. Moreover, one or more of the tasks shown and described in the context of FIG. 6 could be omitted from a practical embodiment of the meal detection process 600 as long as the intended overall functionality remains intact.

In exemplary embodiments, the meal detection process 600 is implemented or otherwise performed by server 106, for example, to detect or otherwise identify unannounced meals to facilitate generating GUI displays, notifications or alerts, or otherwise analyzing a patient's meal response. In some embodiments, the meal detection process 600 may be performed by the server 106 in response to receiving uploaded measurement data from the infusion device 102 and/or the sensing arrangement 104 to detect or otherwise identify a meal substantially in real-time. In other embodiments, the meal detection process 600 may be performed on a periodic basis independent of the infusion device 102 and/or the sensing arrangement 104, for example, on a daily basis, a weekly basis, a monthly basis, or the like.

The meal detection process 600 begins by receiving or otherwise obtaining sensor glucose measurement values associated with a patient, determining sensor glucose measurement statistics associated with a preceding analysis interval, and determining a meal probability value for the preceding analysis interval (tasks 602, 604, 606). In this regard, the server 106 obtains sensor glucose measurement values that are not accompanied by a meal indication, and calculates or otherwise determines sensor glucose measurement statistics based on the sensor glucose measurement values corresponding to an analysis interval preceding the latest or most recent measurement value. For example, continuing the above example, the server 106 calculates sensor glucose measurement statistics based on the sensor glucose measurement values for the hour preceding the current sensor glucose measurement value being analyzed in a similar manner as described above (e.g., task 208). The server 106 also determines a meal probability value based on an average of the meal probability intervals over the one hour interval preceding the current sensor glucose measurement value in a similar manner as described above (e.g., task 210).

After determining sensor glucose measurement statistics and a meal probability value for an interval of sensor glucose measurement values to be analyzed, the meal detection process 600 obtains the meal detection model associated with the patient being analyzed and applies the detection model to the predictive subset of the sensor glucose measurement statistics and meal probability value to determine a metric indicative of whether the current analysis interval corresponds to a meal or non-meal segment (tasks 608, 610). In this regard, the server 106 implements the equation defined by the meal detection model associated with the identifier(s) for the patient being analyzed using current values for the predictive sensor glucose measurement statistic subset identified by the model and the current meal probability value (if indicated as predictive by the model) to obtain a result that quantifies or otherwise characterizes the likelihood of the patient having consumed a meal concurrently or contemporaneously to the current analysis interval. Alternatively, in instances where the patient does not have a patient-specific model assigned, the server 106 may utilize a patient group meal detection model corresponding to a patient group the patient is associated with.

Based on the output of the model, the meal detection process 600 determines whether the current analysis interval corresponds to a meal response by the patient being analyzed, and in response to detecting a meal, the meal detection process 600 provides indication of a meal associated with the current analysis interval (tasks 612, 614). In some embodiments, when the model output indicates the current analysis interval corresponds to a meal segment, the server 106 may analyze the patient's bolus data corresponding to the analysis interval to verify whether a meal bolus identified by the patient (e.g., a bolus accompanied by an input carbohydrate amount or other identification of a meal) was delivered during the analysis interval. When the patient's bolus data includes a bolus delivered during the analysis interval that is not marked as a meal bolus, the server 106 may flag, mark, or otherwise store an indication of a meal bolus in association with that bolus. Additionally, in some embodiments, where the model is capable of being utilized to classify a type of bolus delivered, the server 106 may also store an indication of a bolus type associated with that meal bolus. In some embodiments, in the absence of any bolus delivered during the analysis interval, the server 106 may store an indication of a bolus in association with one or more sensor glucose measurement values or the time period corresponding to the analysis interval to thereby flag, tag, or otherwise mark the analysis interval as a meal segment with a corresponding meal having been consumed by the patient. For example, in one embodiment, the server 106 calculates, estimates, or otherwise determines a time associated with consumption of the meal based on the sensor glucose measurements of the analysis interval and then creates or otherwise generates a meal indication associated with the patient having an associated timestamp corresponding to the estimated time of meal consumption. In this regard, the server 106 may update the patient's historical bolus data to indicate the meal associated with the analysis interval that was detected by the server 106 using the patient's meal detection model.

In response to detecting a meal, in addition to updating the patient's bolus history, the server 106 may update one or more GUI displays to reflect the meal, generate an alert or user notification based on the meal, or initiate or perform some other action in response to the meal. For example, if a monitoring GUI display depicting a graphical representation of the patient's sensor glucose is presented on a device 102, 110 within the patient management system 100, the server 106 may update the GUI display to include a marker for a meal bolus at a time corresponding to the analysis interval, such as for example, at the time of a sensor glucose measurement value of the analysis interval (e.g., the time of the lowest sensor glucose measurement value) or another timestamp assigned to the meal bolus. Thus, a pattern guidance display depicting event patterns detected during operation of the infusion device 102 may depict an event pattern that is influenced by the detected meal and includes a graphical indication of the detected meal associated with a time of day corresponding to the analysis interval, as described in greater detail below in the context of FIG. 7. In yet other embodiments, the meal indication may be utilized to temporarily alter or influence operation of the infusion device 102 (e.g., to modify insulin delivery to account for the meal and/or bolus) as appropriate.

It should be noted that in general, an individual's blood sugar levels are generally influenced by food, exercise, medicine, sleep, and physiological stress (e.g., illness, mental stress, or the like). Accordingly, by virtue of the meal detection process 600 detecting a meal that could otherwise go unannounced or without indication by a user, other pattern detection algorithms can use this additional knowledge of meal consumption to better understand the patient's condition to provide recommendations or guidance for post-meal control, such as, for example, recommended medication regimen, eating habits or nutritional guidance, recommended proper medication types, or other behavioral profiling based on eating habits.

It should be noted that the meal detection process 600 may be incrementally performed on sensor glucose measurement values to classify or otherwise categorize as many non-overlapping segments of the patient history as meal or non-meal segments for use in analyzing the patient's meal response, validating the meal detection model, or the like. In this regard, when a meal bolus is manually-indicated or announced, the meal detection process 600 may still be performed to verify or otherwise confirm that the meal detection model generates an output indicative of a meal. For example, in one or more embodiment, the server 106 may dynamically update or track the performance of the model over time and detect when one or more performance metrics associated with the model fail to satisfy the validation criteria (e.g., task 218). In this regard, when the model performance suffers, the patient modeling process 200 may be repeated to update the patient's meal detection model or reassign the patient to a population model as described above.

Figure 7:
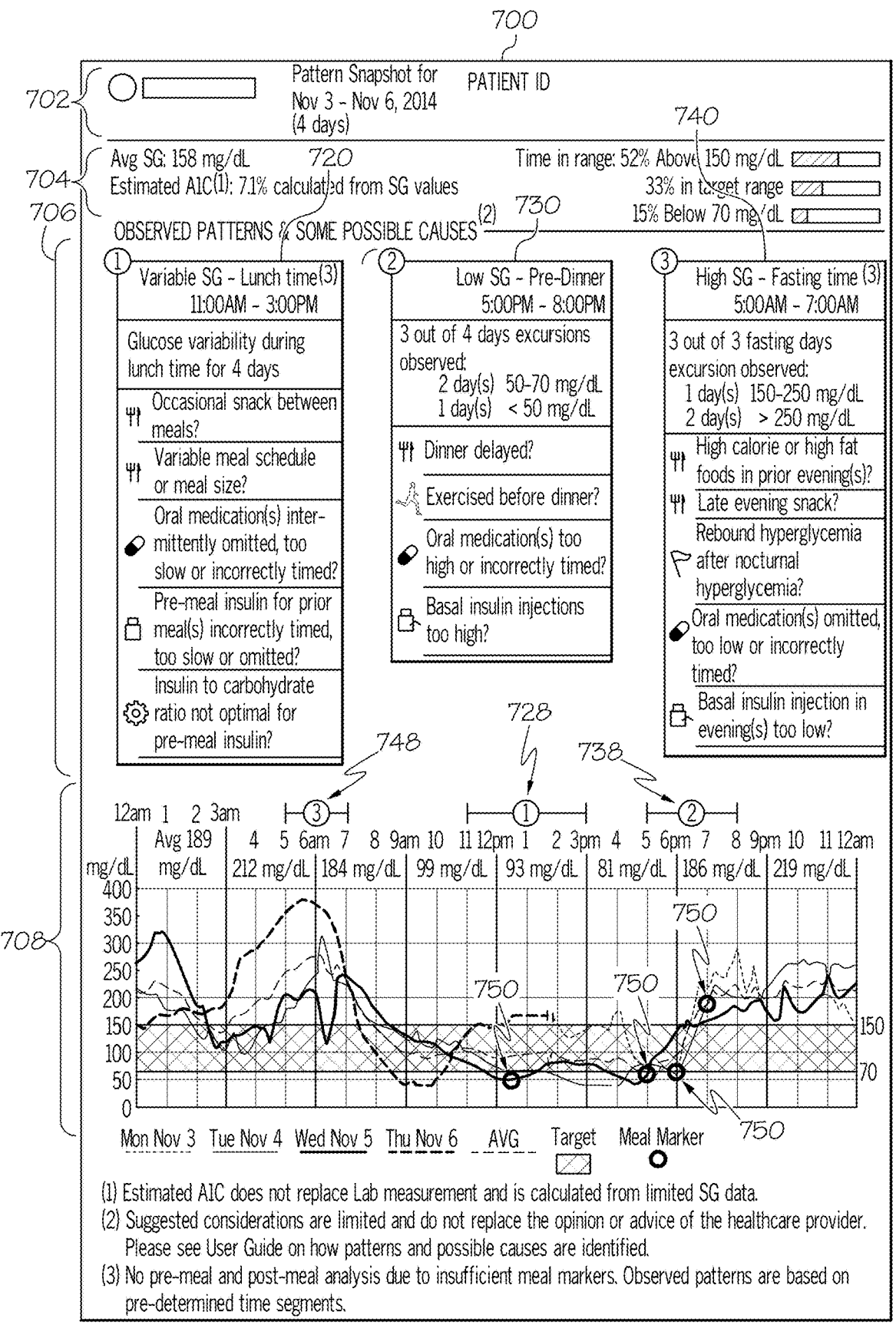
FIG. 7 depicts an exemplary embodiment of a snapshot graphical user interface (GUI) display that may be presented on a display device associated with a computing device in one or more embodiments.

FIG. 7 depicts an exemplary embodiment of a snapshot GUI display 700 or report that may be presented on a display device associated with an electronic device 102, 106, 110 in the patient management system 100 in conjunction with the meal detection process 600 described above. The snapshot GUI display 700 includes a plurality of regions 702, 704, 706, 708 that present information pertaining to past operation of the infusion device 102 to deliver insulin to regulate the glucose level of a diabetic patient. A header region 702 is presented at the top of the snapshot GUI display 700 and includes a graphical representation of a preceding time period of operation (e.g., November 3-November 6) associated with the snapshot GUI display 700 for which information is presented in the below regions 704, 706, 708. A performance metric region 704 is presented below the header region 702 and includes graphical representations or other indicia of the values for various performance metrics calculated based on the historical measurement data for the patient's glucose level over the time period associated with the snapshot GUI display 700, such as, for example, an average sensor glucose measurement value, an estimated A1C level, estimated percentages of the snapshot time period during which durations the sensor glucose measurement values were above, below or between one or more glucose threshold values, and the like.

The illustrated snapshot GUI display 700 includes a graph overlay region 708 presented at the bottom of the snapshot GUI display 700 that includes graphical representations of historical measurement data for the patient's glucose level over the snapshot time period with respect to time. In this regard, the graph overlay region 708 may include a line graph including a line associated with each day within the snapshot time period that depicts the patient's sensor glucose measurements values from that day with respect to time of day. Additionally, the graph overlay region 708 may include a line representative of the average of the patient's sensor glucose measurements across the different days within the snapshot time period with respect to time of day. The illustrated graph overlay region 708 also includes a visually distinguishable overlay region that indicates a target range for the patient's sensor glucose measurement values. In exemplary embodiments, the graphical representation of the measurements for each different day or date depicted on the graph overlay region 708 is rendered with a unique color or other visually distinguishable characteristic relative to the graphical representations corresponding to other days or dates, with the meal markers 750 on that respective day or date also being rendered in the same color or visually distinguishable characteristic and placed on the line corresponding to that respective day or date.

Referring now to FIGS. 6-7, in accordance with one or more embodiments, one or more of the meal markers 750 are generated in response to the meal detection process 600 detecting a meal segment within the historical measurement data for the patient's glucose level over the snapshot time period. For example, the meal detection process 600 may detect a meal segment corresponding to the period of 12:30 PM-1:30 PM of the patient's measurement data for November 5$^{th}$, and in response, the meal detection process 600 may store or otherwise provide an indication of a meal associated with the sensor glucose measurement value corresponding to the start of that meal segment the absence of a meal indication within the patient's bolus history. Thus, even if the patient does not manually provide the meal indication, a corresponding meal marker 750 for that meal may still be presented on the snapshot GUI display 700.

The illustrated snapshot GUI display 700 also includes a pattern detection region 706 that includes a plurality of pattern guidance displays 720, 730, 740, where each pattern guidance display 720, 730, 740 corresponds to a respective pattern of events identified during the snapshot time period based on the patient's sensor glucose measurement values for the snapshot time period. In this regard, the historical sensor glucose measurement values are analyzed for different monitoring periods within the snapshot time period.

Here, it is noted that the meal indications generated by the meal detection process 600 may be utilized to delineate or otherwise determine the times or portions of the day corresponding to monitoring periods referenced to meals. For example, the meal marker 750 identified based on the period of 12:30 PM-1:30 PM of the patient's measurement data for November 5$^{th}$ may be utilized to determine one or more of a starting time, an ending time, or a duration of a lunch time monitoring period in a manner that ensures the lunch time monitoring period includes or otherwise encompasses the meal detected by the meal detection process 600. Thus, patterns for meal time monitoring period may be identified and analyzed even if the patient does not manually provide a meal indication for that particular meal. For example, a patient may routinely or habitually fail to manually indicate when he or she has consumed lunch due to the patient being preoccupied with other daily activities. By virtue of the patient-specific meal detection described above, lunch time event patterns for that patient may be better identified by tailoring the lunch time monitoring period to fit the patient's midday meal times. Thus, the duration of the lunch time monitoring period depicted by the lunch time monitoring period marker 728 described below encompasses the meal marker 750 detected by the meal detection process 600.

Based on the subset of sensor glucose measurement values associated with times of day within a respective monitoring period, a pattern of one or more events is detected or otherwise identified within that monitoring period, such as, for example, a glucose variability event, a high glucose (or hyperglycemic) event, or a low glucose (or hypoglycemic) event. When a plurality of event patterns are identified, the identified event patterns are prioritized and filtered to limit the number of event patterns for display. For example, in one embodiment, the detected event patterns are prioritized primarily based on event type (e.g., from most significant to least significant) and secondarily based on the monitoring period associated with the respective event pattern, and then filtered to remove lower priority event patterns above a display threshold that limits the number of displayed event patterns.

For each remaining event pattern of the filtered prioritized list, a pattern guidance display 720, 730, 740 may be generated that includes graphical indicia of the event type and the monitoring period associated with the detected pattern, graphical indicia of the number, frequency, severity, or other characteristics of the events associated with the detected pattern, graphical indicia of potential causes or remedial actions for the detected events, and the like, which may also be prioritized or ordered according to their respective clinical relevance. Additionally, in exemplary embodiments, graphical indicia 728, 738, 748 of the detected event patterns are presented within the graph overly region 708 in a manner that establishes an association between the detected event pattern, the time of day associated with its corresponding monitoring period, and its relative priority level. Thus, the graphical indicia 728, 738, 748 facilitate establishing an association between a respective subset of the historical measurement data presented within the graph overlay region 708 and a corresponding event pattern detected based on that subset of historical measurement data. For example, in the illustrated embodiment of FIG. 7, a marker 728 is presented overlying the graph overlay region 708 that includes an identifier that indicates the detected event pattern the marker 728 corresponds to (e.g., number 1 to indicate the highest priority event pattern 720), and the marker 728 has a width or other dimension that encompasses or otherwise corresponds to the subset of the sensor glucose measurement values associated with the time of day corresponding to the monitoring period associated with the detected event pattern (e.g., the lunch time period).

Figure 8:
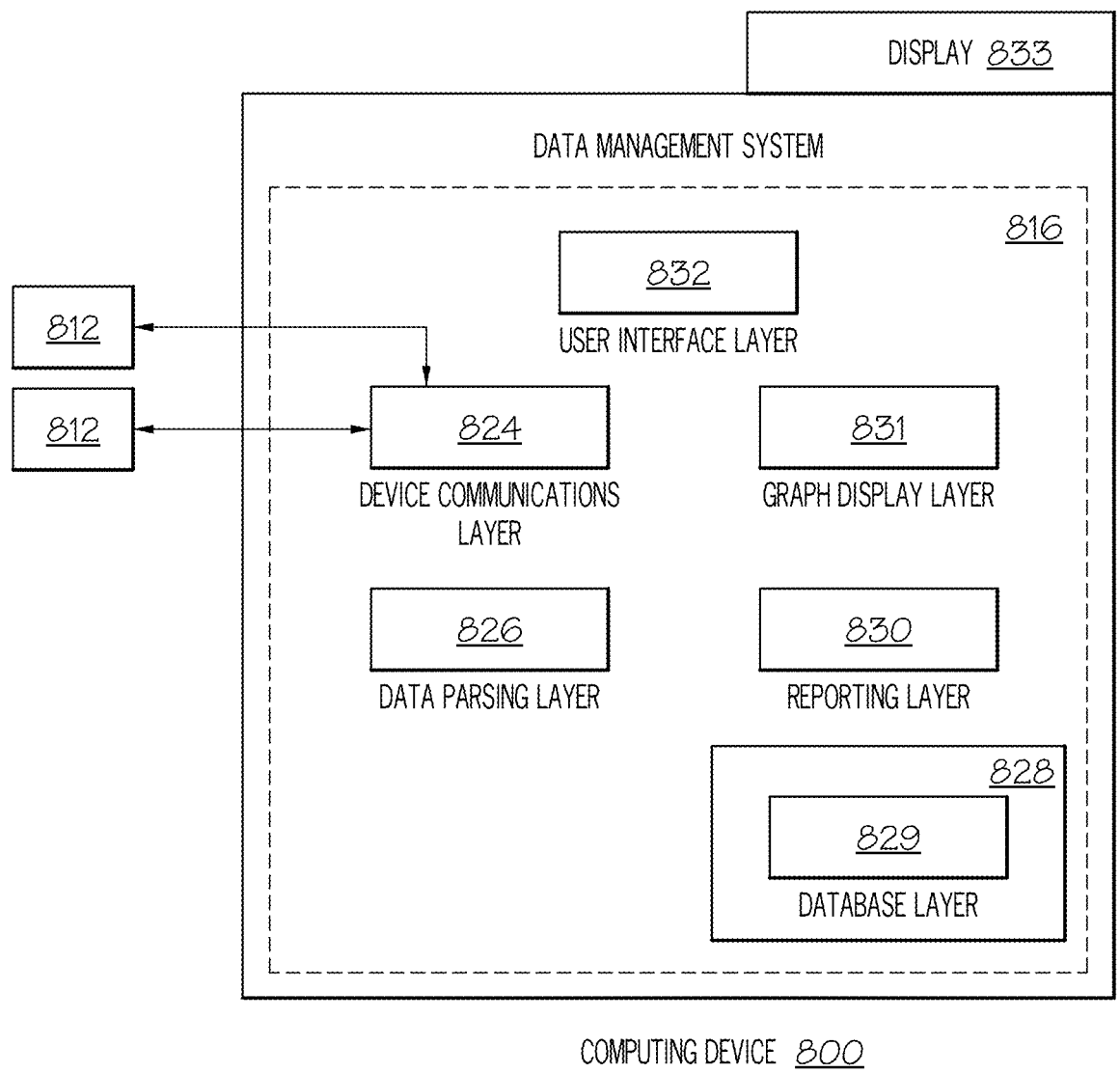
FIG. 8 depicts an embodiment of a computing device for a diabetes data management system in accordance with one or more embodiments.

FIG. 8 illustrates a computing device 800 including a display 833 suitable for presenting a snapshot GUI display 700 as part of a diabetes data management system in conjunction with the processes 200, 600 of FIGS. 2 and 6 described above. The diabetes data management system (DDMS) may be referred to as the Medtronic MiniMed CARELINK™ system or as a medical data management system (MDMS) in some embodiments. The DDMS may be housed on a server or a plurality of servers which a user or a health care professional may access via a communications network via the Internet or the World Wide Web. Some models of the DDMS, which is described as an MDMS, are described in U.S. Patent Application Publication Nos. 2006/0031094 and 2013/0338630, which is herein incorporated by reference in their entirety.

While description of embodiments are made in regard to monitoring medical or biological conditions for subjects having diabetes, the systems and processes herein are applicable to monitoring medical or biological conditions for cardiac subjects, cancer subjects, HIV subjects, subjects with other disease, infection, or controllable conditions, or various combinations thereof.

In various embodiments, the DDMS may be installed in a computing device in a health care provider's office, such as a doctor's office, a nurse's office, a clinic, an emergency room, an urgent care office. Health care providers may be reluctant to utilize a system where their confidential patient data is to be stored in a computing device such as a server on the Internet.

The DDMS may be installed on a computing device 800. The computing device 800 may be coupled to a display 833. In some embodiments, the computing device 800 may be in a physical device separate from the display (such as in a personal computer, a mini-computer, etc.) In some embodiments, the computing device 800 may be in a single physical enclosure or device with the display 833 such as a laptop where the display 833 is integrated into the computing device. In various embodiments, the computing device 800 hosting the DDMS may be, but is not limited to, a desktop computer, a laptop computer, a server, a network computer, a personal digital assistant (PDA), a portable telephone including computer functions, a pager with a large visible display, an insulin pump including a display, a glucose sensor including a display, a glucose meter including a display, and/or a combination insulin pump/glucose sensor having a display. The computing device may also be an insulin pump coupled to a display, a glucose meter coupled to a display, or a glucose sensor coupled to a display. The computing device 800 may also be a server located on the Internet that is accessible via a browser installed on a laptop computer, desktop computer, a network computer, or a PDA. The computing device 800 may also be a server located in a doctor's office that is accessible via a browser installed on a portable computing device, e.g., laptop, PDA, network computer, portable phone, which has wireless capabilities and can communicate via one of the wireless communication protocols such as Bluetooth and IEEE 802.11 protocols.

In the embodiment shown in FIG. 8, the data management system 816 comprises a group of interrelated software modules or layers that specialize in different tasks. The system software includes a device communication layer 824, a data parsing layer 826, a database layer 828, database storage devices 829, a reporting layer 830, a graph display layer 831, and a user interface layer 832. The diabetes data management system may communicate with a plurality of subject support devices 812, two of which are illustrated in FIG. 8. Although the different reference numerals refer to a number of layers, (e.g., a device communication layer, a data parsing layer, a database layer), each layer may include a single software module or a plurality of software modules. For example, the device communications layer 824 may include a number of interacting software modules, libraries, etc. In some embodiments, the data management system 816 may be installed onto a non-volatile storage area (memory such as flash memory, hard disk, removable hard, DVD-RW, CD-RW) of the computing device 800. If the data management system 816 is selected or initiated, the system 816 may be loaded into a volatile storage (memory such as DRAM, SRAM, RAM, DDRAM) for execution.

The device communication layer 824 is responsible for interfacing with at least one, and, in further embodiments, to a plurality of different types of subject support devices 812, such as, for example, blood glucose meters, glucose sensors/monitors, or an infusion pump. In one embodiment, the device communication layer 824 may be configured to communicate with a single type of subject support device 812. However, in more comprehensive embodiments, the device communication layer 824 is configured to communicate with multiple different types of subject support devices 812, such as devices made from multiple different manufacturers, multiple different models from a particular manufacturer and/or multiple different devices that provide different functions (such as infusion functions, sensing functions, metering functions, communication functions, user interface functions, or combinations thereof). By providing an ability to interface with multiple different types of subject support devices 812, the diabetes data management system 816 may collect data from a significantly greater number of discrete sources. Such embodiments may provide expanded and improved data analysis capabilities by including a greater number of subjects and groups of subjects in statistical or other forms of analysis that can benefit from larger amounts of sample data and/or greater diversity in sample data, and, thereby, improve capabilities of determining appropriate treatment parameters, diagnostics, or the like.

The device communication layer 824 allows the DDMS 816 to receive information from and transmit information to or from each subject support device 812 in the system 816. Depending upon the embodiment and context of use, the type of information that may be communicated between the system 816 and device 812 may include, but is not limited to, data, programs, updated software, education materials, warning messages, notifications, device settings, therapy parameters, or the like. The device communication layer 824 may include suitable routines for detecting the type of subject support device 812 in communication with the system 816 and implementing appropriate communication protocols for that type of device 812. Alternatively or in addition, the subject support device 812 may communicate information in packets or other data arrangements, where the communication includes a preamble or other portion that includes device identification information for identifying the type of the subject support device. Alternatively, or in addition, the subject support device 812 may include suitable user-operable interfaces for allowing a user to enter information, such as by selecting an optional icon or text or other device identifier, that corresponds to the type of subject support device used by that user. Such information may be communicated to the system 816, through a network connection. In yet further embodiments, the system 816 may detect the type of subject support device 812 it is communicating with and then may send a message requiring the user to verify that the system 816 properly detected the type of subject support device being used by the user. For systems 816 that are capable of communicating with multiple different types of subject support devices 812, the device communication layer 824 may be capable of implementing multiple different communication protocols and selects a protocol that is appropriate for the detected type of subject support device.

The data-parsing layer 826 is responsible for validating the integrity of device data received and for inputting it correctly into a database 829. A cyclic redundancy check CRC process for checking the integrity of the received data may be employed. Alternatively, or in addition, data may be received in packets or other data arrangements, where preambles or other portions of the data include device type identification information. Such preambles or other portions of the received data may further include device serial numbers or other identification information that may be used for validating the authenticity of the received information. In such embodiments, the system 816 may compare received identification information with pre-stored information to evaluate whether the received information is from a valid source.

The database layer 828 may include a centralized database repository that is responsible for warehousing and archiving stored data in an organized format for later access, and retrieval. The database layer 828 operates with one or more data storage device(s) 829 suitable for storing and providing access to data in the manner described herein. Such data storage device(s) 829 may comprise, for example, one or more hard discs, optical discs, tapes, digital libraries or other suitable digital or analog storage media and associated drive devices, drive arrays or the like.

Data may be stored and archived for various purposes, depending upon the embodiment and environment of use. Information regarding specific subjects and patient support devices may be stored and archived and made available to those specific subjects, their authorized healthcare providers and/or authorized healthcare payor entities for analyzing the subject's condition. Also, certain information regarding groups of subjects or groups of subject support devices may be made available more generally for healthcare providers, subjects, personnel of the entity administering the system 816 or other entities, for analyzing group data or other forms of conglomerate data.

Embodiments of the database layer 828 and other components of the system 816 may employ suitable data security measures for securing personal medical information of subjects, while also allowing non-personal medical information to be more generally available for analysis. Embodiments may be configured for compliance with suitable government regulations, industry standards, policies or the like, including, but not limited to the Health Insurance Portability and Accountability Act of 1996 (HIPAA).

The database layer 828 may be configured to limit access of each user to types of information pre-authorized for that user. For example, a subject may be allowed access to his or her individual medical information (with individual identifiers) stored by the database layer 828, but not allowed access to other subject's individual medical information (with individual identifiers). Similarly, a subject's authorized healthcare provider or payor entity may be provided access to some or all of the subject's individual medical information (with individual identifiers) stored by the database layer 828, but not allowed access to another individual's personal information. Also, an operator or administrator-user (on a separate computer communicating with the computing device 800) may be provided access to some or all subject information, depending upon the role of the operator or administrator. On the other hand, a subject, healthcare provider, operator, administrator or other entity, may be authorized to access general information of unidentified individuals, groups or conglomerates (without individual identifiers) stored by the database layer 828 in the data storage devices 829.

In embodiments of the subject matter described herein, the database layer 828 may store patient-specific event detection models, population group detection models, and individual patient preference profiles. In the database layer 828, for example, each user may store information regarding specific parameters that correspond to the user. Illustratively, these parameters could include target blood glucose or sensor glucose levels, what type of equipment the users utilize (insulin pump, glucose sensor, blood glucose meter, etc.) and could be stored in a record, a file, or a memory location in the data storage device(s) 829 in the database layer. The preference profiles may include various threshold values, monitoring period values, prioritization criteria, filtering criteria, and/or other user-specific values for parameters utilized to generate a snapshot GUI display, such as snapshot GUI display 700, on the display 833 or a support device 812 in a personalized or patient-specific manner. Additionally, data or information defining the meal detection or other event detection models associated with a particular individual may also be stored in a record, a file, or a memory location associated with that patient in the data storage device(s) 829 in the database layer.

The DDMS 816 may measure, analyze, and track either blood glucose (BG) or sensor glucose (SG) readings for a user. In exemplary embodiments, the medical data management system may measure, track, or analyze both BG and SG readings for the user. Accordingly, although certain reports may mention or illustrate BG or SG only, the reports may monitor and display results for the other one of the glucose readings or for both of the glucose readings.

The reporting layer 830 may include a report wizard program that pulls data from selected locations in the database 829 and generates report information from the desired parameters of interest. The reporting layer 830 may be configured to generate multiple different types of reports, each having different information and/or showing information in different formats (arrangements or styles), where the type of report may be selectable by the user. A plurality of pre-set types of report (with pre-defined types of content and format) may be available and selectable by a user. At least some of the pre-set types of reports may be common, industry standard report types with which many healthcare providers should be familiar. In exemplary embodiments described herein, the reporting layer 830 also facilitates generation of a snapshot report including a snapshot GUI display, such as snapshot GUI display 700 of FIG. 7.

In some embodiments, the database layer 828 may calculate values for various medical information that is to be displayed on the reports generated by the report or reporting layer 830. For example, the database layer 828, may calculate average blood glucose or sensor glucose readings for specified timeframes. In some embodiments, the reporting layer 830 may calculate values for medical or physical information that is to be displayed on the reports. For example, a user may select parameters which are then utilized by the reporting layer 830 to generate medical information values corresponding to the selected parameters. In other embodiments, the user may select a parameter profile that previously existed in the database layer 828.

Alternatively, or in addition, the report wizard may allow a user to design a custom type of report. For example, the report wizard may allow a user to define and input parameters (such as parameters specifying the type of content data, the time period of such data, the format of the report, or the like) and may select data from the database and arrange the data in a printable or displayable arrangement, based on the user-defined parameters. In further embodiments, the report wizard may interface with or provide data for use by other programs that may be available to users, such as common report generating, formatting or statistical analysis programs. In this manner, users may import data from the system 816 into further reporting tools familiar to the user. The reporting layer 830 may generate reports in displayable form to allow a user to view reports on a standard display device, printable form to allow a user to print reports on standard printers, or other suitable forms for access by a user. Embodiments may operate with conventional file format schemes for simplifying storing, printing and transmitting functions, including, but not limited to PDF, JPEG, or the like. Illustratively, a user may select a type of report and parameters for the report and the reporting layer 830 may create the report in a PDF format. A PDF plug-in may be initiated to help create the report and also to allow the user to view the report. Under these operating conditions, the user may print the report utilizing the PDF plug-in. In certain embodiments in which security measures are implemented, for example, to meet government regulations, industry standards or policies that restrict communication of subject's personal information, some or all reports may be generated in a form (or with suitable software controls) to inhibit printing, or electronic transfer (such as a non-printable and/or non-capable format). In yet further embodiments, the system 816 may allow a user generating a report to designate the report as non-printable and/or non-transferable, whereby the system 816 will provide the report in a form that inhibits printing and/or electronic transfer.

The reporting layer 830 may transfer selected reports to the graph display layer 831. The graph display layer 831 receives information regarding the selected reports and converts the data into a format that can be displayed or shown on a display 833.

In various embodiments, the reporting layer 830 may store a number of the user's parameters. Illustratively, the reporting layer 830 may store the type of carbohydrate units, a blood glucose movement or sensor glucose reading, a carbohydrate conversion factor, and timeframes for specific types of reports. These examples are meant to be illustrative and not limiting.

Data analysis and presentations of the reported information may be employed to develop and support diagnostic and therapeutic parameters. Where information on the report relates to an individual subject, the diagnostic and therapeutic parameters may be used to assess the health status and relative well-being of that subject, assess the subject's compliance to a therapy, as well as to develop or modify treatment for the subject and assess the subject's behaviors that affect his/her therapy. Where information on the report relates to groups of subjects or conglomerates of data, the diagnostic and therapeutic parameters may be used to assess the health status and relative well-being of groups of subjects with similar medical conditions, such as, but not limited to, diabetic subjects, cardiac subjects, diabetic subjects having a particular type of diabetes or cardiac condition, subjects of a particular age, sex or other demographic group, subjects with conditions that influence therapeutic decisions such as but not limited to pregnancy, obesity, hypoglycemic unawareness, learning disorders, limited ability to care for self, various levels of insulin resistance, combinations thereof, or the like.

The user interface layer 832 supports interactions with the end user, for example, for user login and data access, software navigation, data input, user selection of desired report types and the display of selected information. Users may also input parameters to be utilized in the selected reports via the user interface layer 832. Examples of users include but are not limited to: healthcare providers, healthcare payer entities, system operators or administrators, researchers, business entities, healthcare institutions and organizations, or the like, depending upon the service being provided by the system and depending upon the embodiment. More comprehensive embodiments are capable of interacting with some or all of the above-noted types of users, wherein different types of users have access to different services or data or different levels of services or data.

In an example embodiment, the user interface layer 832 provides one or more websites accessible by users on the Internet. The user interface layer may include or operate with at least one (or multiple) suitable network server(s) to provide the website(s) over the Internet and to allow access, world-wide, from Internet-connected computers using standard Internet browser software. The website(s) may be accessed by various types of users, including but not limited to subjects, healthcare providers, researchers, business entities, healthcare institutions and organizations, payor entities, pharmaceutical partners or other sources of pharmaceuticals or medical equipment, and/or support personnel or other personnel running the system 816, depending upon the embodiment of use.

In another example embodiment, where the DDMS 816 is located on one computing device 800, the user interface layer 832 provides a number of menus to the user to navigate through the DDMS. These menus may be created utilizing any menu format, including but not limited to HTML, XML, or Active Server pages. A user may access the DDMS 816 to perform one or more of a variety of tasks, such as accessing general information made available on a website to all subjects or groups of subjects. The user interface layer 832 of the DDMS 816 may allow a user to access specific information or to generate reports regarding that subject's medical condition or that subject's medical device(s) 812, to transfer data or other information from that subject's support device(s) 812 to the system 816, to transfer data, programs, program updates or other information from the system 816 to the subject's support device(s) 812, to manually enter information into the system 816, to engage in a remote consultation exchange with a healthcare provider, or to modify the custom settings in a subject's supported device and/or in a subject's DDMS/MDMS data file.

The system 816 may provide access to different optional resources or activities (including accessing different information items and services) to different users and to different types or groups of users, such that each user may have a customized experience and/or each type or group of user (e.g., all users, diabetic users, cardio users, healthcare provider-user or payor-user, or the like) may have a different set of information items or services available on the system. The system 816 may include or employ one or more suitable resource provisioning program or system for allocating appropriate resources to each user or type of user, based on a pre-defined authorization plan. Resource provisioning systems are well known in connection with provisioning of electronic office resources (email, software programs under license, sensitive data, etc.) in an office environment, for example, in a local area network LAN for an office, company or firm. In one example embodiment, such resource provisioning systems is adapted to control access to medical information and services on the DDMS 816, based on the type of user and/or the identity of the user.

Upon entering successful verification of the user's identification information and password, the user may be provided access to secure, personalized information stored on the DDMS 816. For example, the user may be provided access to a secure, personalized location in the DDMS 816 which has been assigned to the subject. This personalized location may be referred to as a personalized screen, a home screen, a home menu, a personalized page, etc. The personalized location may provide a personalized home screen to the subject, including selectable icons or menu items for selecting optional activities, including, for example, an option to transfer device data from a subject's supported device 812 to the system 816, manually enter additional data into the system 816, modify the subject's custom settings, and/or view and print reports. Reports may include data specific to the subject's condition, including but not limited to, data obtained from the subject's subject support device(s) 812, data manually entered, data from medical libraries or other networked therapy management systems, data from the subjects or groups of subjects, or the like. Where the reports include subject-specific information and subject identification information, the reports may be generated from some or all subject data stored in a secure storage area (e.g., storage devices 829) employed by the database layer 828.

The user may select an option to transfer (send) device data to the medical data management system 816. If the system 816 receives a user's request to transfer device data to the system, the system 816 may provide the user with step-by-step instructions on how to transfer data from the subject's supported device(s) 812. For example, the DDMS 816 may have a plurality of different stored instruction sets for instructing users how to download data from different types of subject support devices, where each instruction set relates to a particular type of subject supported device (e.g., pump, sensor, meter, or the like), a particular manufacturer's version of a type of subject support device, or the like. Registration information received from the user during registration may include information regarding the type of subject support device(s) 812 used by the subject. The system 816 employs that information to select the stored instruction set(s) associated with the particular subject's support device(s) 812 for display to the user.

Other activities or resources available to the user on the system 816 may include an option for manually entering information to the DDMS/MDMS 816. For example, from the user's personalized menu or location, the user may select an option to manually enter additional information into the system 816.

Further optional activities or resources may be available to the user on the DDMS 816. For example, from the user's personalized menu, the user may select an option to receive data, software, software updates, treatment recommendations or other information from the system 816 on the subject's support device(s) 812. If the system 816 receives a request from a user to receive data, software, software updates, treatment recommendations or other information, the system 816 may provide the user with a list or other arrangement of multiple selectable icons or other indicia representing available data, software, software updates or other information available to the user.

Yet further optional activities or resources may be available to the user on the medical data management system 816 including, for example, an option for the user to customize or otherwise further personalize the user's personalized location or menu. In particular, from the user's personalized location, the user may select an option to customize parameters for the user. In addition, the user may create profiles of customizable parameters. When the system 816 receives such a request from a user, the system 816 may provide the user with a list or other arrangement of multiple selectable icons or other indicia representing parameters that may be modified to accommodate the user's preferences. When a user selects one or more of the icons or other indicia, the system 816 may receive the user's request and makes the requested modification.

Figure 9:
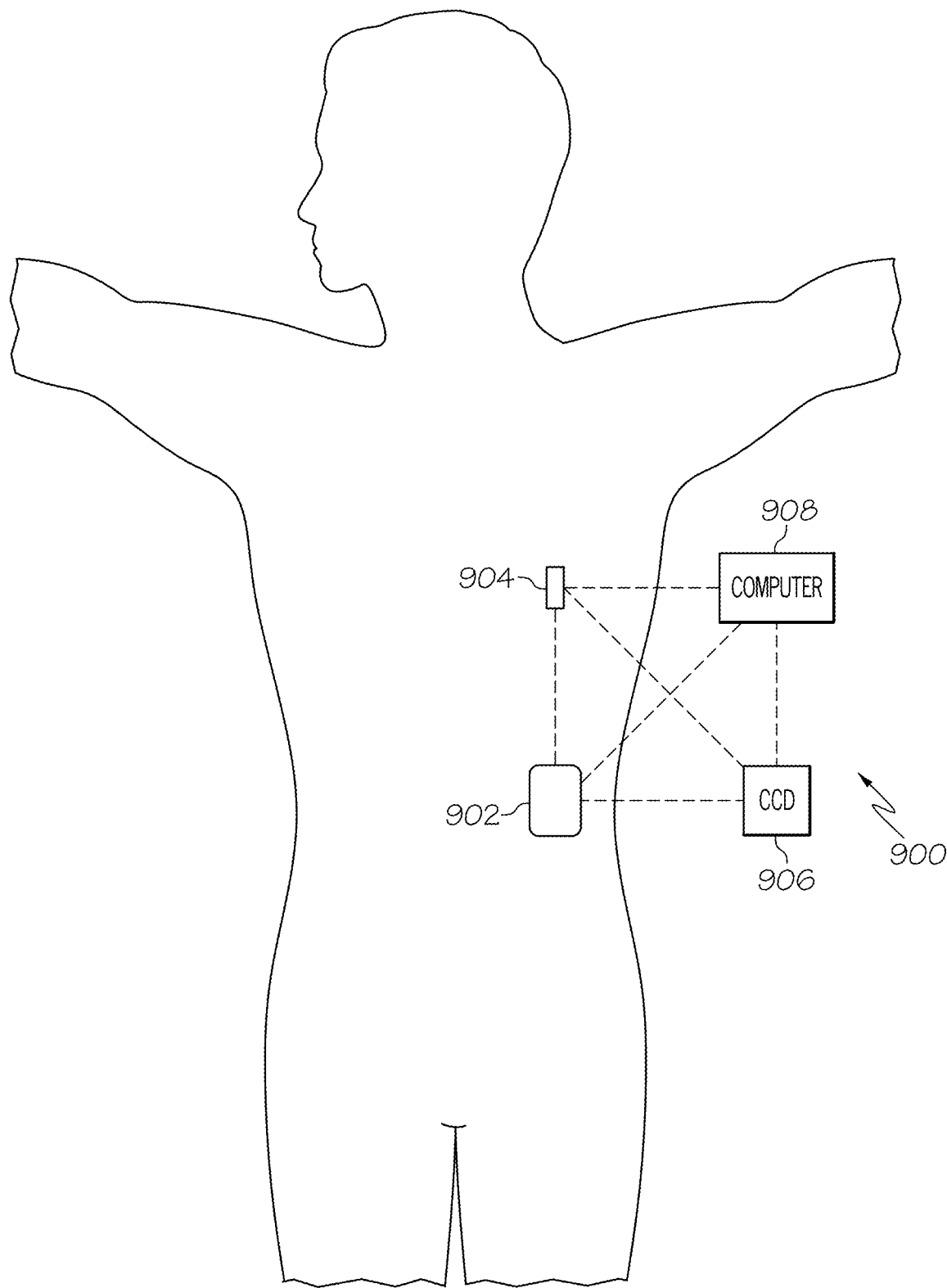
FIG. 9 depicts an exemplary embodiment of an infusion system.

FIG. 9 depicts one exemplary embodiment of an infusion system 900 that includes, without limitation, a fluid infusion device (or infusion pump) 902, a sensing arrangement 904, a command control device (CCD) 906, and a computer 908, which could be realized as any one of the computing devices 106, 110, 800, 812 described above. The components of an infusion system 900 may be realized using different platforms, designs, and configurations, and the embodiment shown in FIG. 9 is not exhaustive or limiting. In practice, the infusion device 902 and the sensing arrangement 904 are secured at desired locations on the body of a user (or patient), as illustrated in FIG. 9. In this regard, the locations at which the infusion device 902 and the sensing arrangement 904 are secured to the body of the user in FIG. 9 are provided only as a representative, non-limiting, example. The elements of the infusion system 900 may be similar to those described in U.S. Pat. No. 8,674,288, the subject matter of which is hereby incorporated by reference in its entirety.

In the illustrated embodiment of FIG. 9, the infusion device 902 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 904 generally represents the components of the infusion system 900 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 904 may include electronics and enzymes reactive to a biological or physiological condition of the user, such as a blood glucose level, or the like, and provide data indicative of the blood glucose level to the infusion device 902, the CCD 906 and/or the computer 908. For example, the infusion device 902, the CCD 906 and/or the computer 908 may include a display for presenting information or data to the user based on the sensor data received from the sensing arrangement 904, such as, for example, a current glucose level of the user, a graph or chart of the user's glucose level versus time, device status indicators, alert messages, or the like. In other embodiments, the infusion device 902, the CCD 906 and/or the computer 908 may include electronics and software that are configured to analyze sensor data and operate the infusion device 902 to deliver fluid to the body of the user based on the sensor data and/or preprogrammed delivery routines. Thus, in exemplary embodiments, one or more of the infusion device 902, the sensing arrangement 904, the CCD 906, and/or the computer 908 includes a transmitter, a receiver, and/or other transceiver electronics that allow for communication with other components of the infusion system 900, so that the sensing arrangement 904 may transmit sensor data or monitor data to one or more of the infusion device 902, the CCD 906 and/or the computer 908.

Still referring to FIG. 9, in various embodiments, the sensing arrangement 904 may be secured to the body of the user or embedded in the body of the user at a location that is remote from the location at which the infusion device 902 is secured to the body of the user. In various other embodiments, the sensing arrangement 904 may be incorporated within the infusion device 902. In other embodiments, the sensing arrangement 904 may be separate and apart from the infusion device 902, and may be, for example, part of the CCD 906. In such embodiments, the sensing arrangement 904 may be configured to receive a biological sample, analyte, or the like, to measure a condition of the user.

In various embodiments, the CCD 906 and/or the computer 908 may include electronics and other components configured to perform processing, delivery routine storage, and to control the infusion device 902 in a manner that is influenced by sensor data measured by and/or received from the sensing arrangement 904. By including control functions in the CCD 906 and/or the computer 908, the infusion device 902 may be made with more simplified electronics. However, in other embodiments, the infusion device 902 may include all control functions, and may operate without the CCD 906 and/or the computer 908. In various embodiments, the CCD 906 may be a portable electronic device. In addition, in various embodiments, the infusion device 902 and/or the sensing arrangement 904 may be configured to transmit data to the CCD 906 and/or the computer 908 for display or processing of the data by the CCD 906 and/or the computer 908.

In some embodiments, the CCD 906 and/or the computer 908 may provide information to the user that facilitates the user's subsequent use of the infusion device 902. For example, the CCD 906 may provide information to the user to allow the user to determine the rate or dose of medication to be administered into the user's body. In other embodiments, the CCD 906 may provide information to the infusion device 902 to autonomously control the rate or dose of medication administered into the body of the user. In some embodiments, the sensing arrangement 904 may be integrated into the CCD 906. Such embodiments may allow the user to monitor a condition by providing, for example, a sample of his or her blood to the sensing arrangement 904 to assess his or her condition. In some embodiments, the sensing arrangement 904 and the CCD 906 may be used for determining glucose levels in the blood and/or body fluids of the user without the use of, or necessity of, a wire or cable connection between the infusion device 902 and the sensing arrangement 904 and/or the CCD 906.

In one or more exemplary embodiments, the sensing arrangement 904 and/or the infusion device 902 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153, all of which are incorporated herein by reference in their entirety. In such embodiments, the sensing arrangement 904 is configured to sense or measure a condition of the user, such as, blood glucose level or the like. The infusion device 902 is configured to deliver fluid in response to the condition sensed by the sensing arrangement 904. In turn, the sensing arrangement 904 continues to sense or otherwise quantify a current condition of the user, thereby allowing the infusion device 902 to deliver fluid continuously in response to the condition currently (or most recently) sensed by the sensing arrangement 904 indefinitely. In some embodiments, the sensing arrangement 904 and/or the infusion device 902 may be configured to utilize the closed-loop system only for a portion of the day, for example only when the user is asleep or awake.

Figure 10:
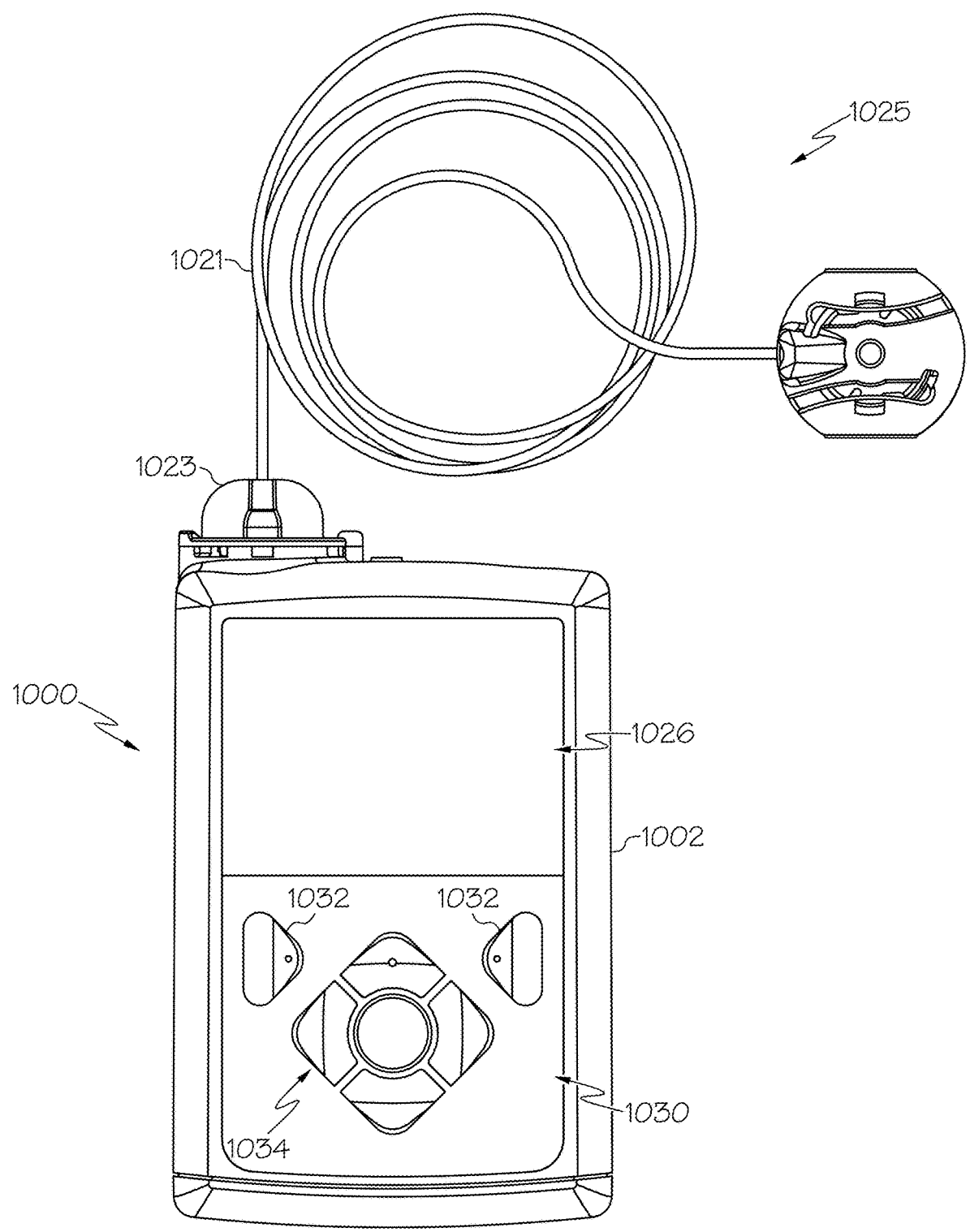
FIG. 10 depicts a plan view of an exemplary embodiment of a fluid infusion device suitable for use in the infusion system of FIG. 9.
Figure 11:
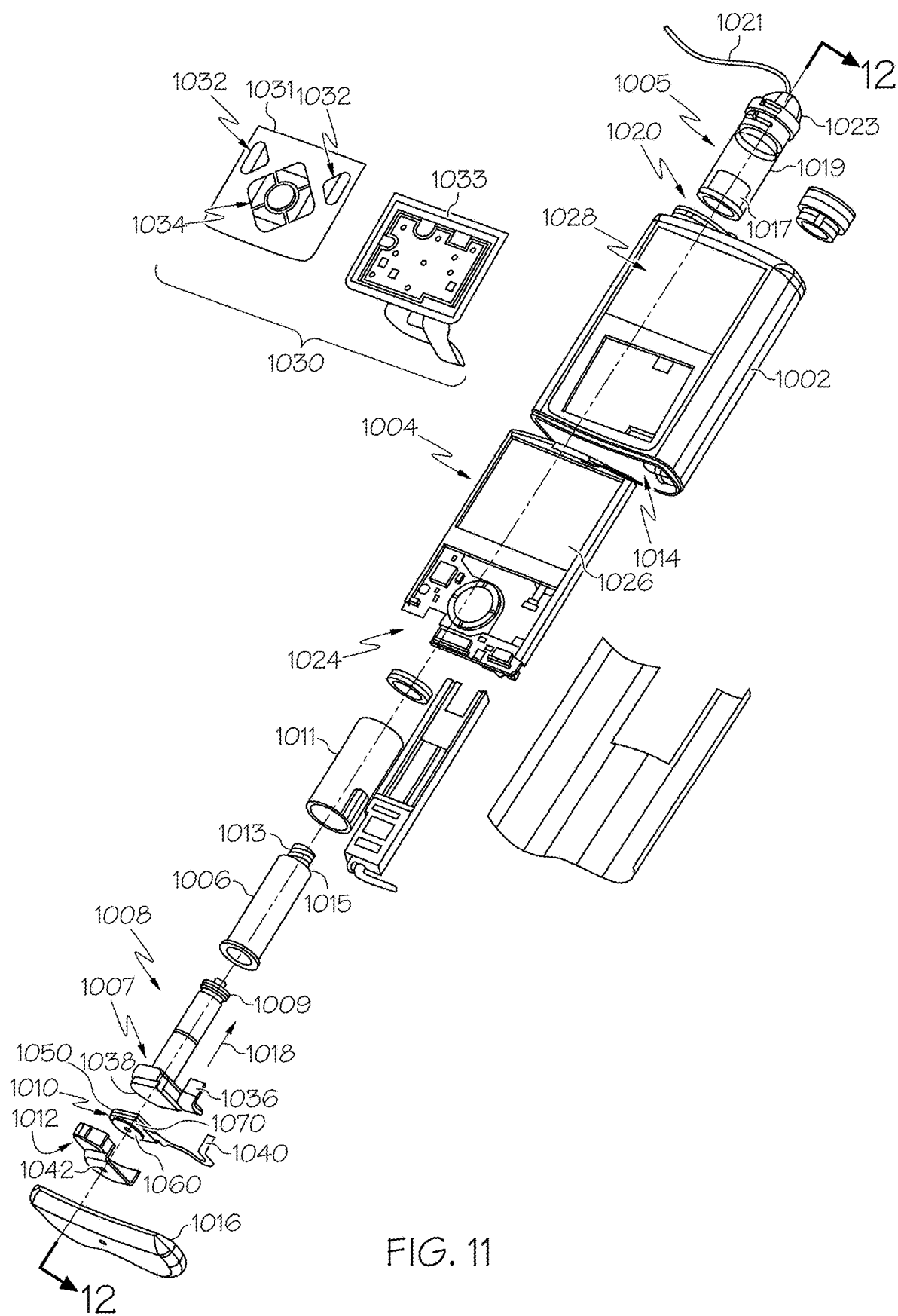
FIG. 11 is an exploded perspective view of the fluid infusion device of FIG. 10.
Figure 12:
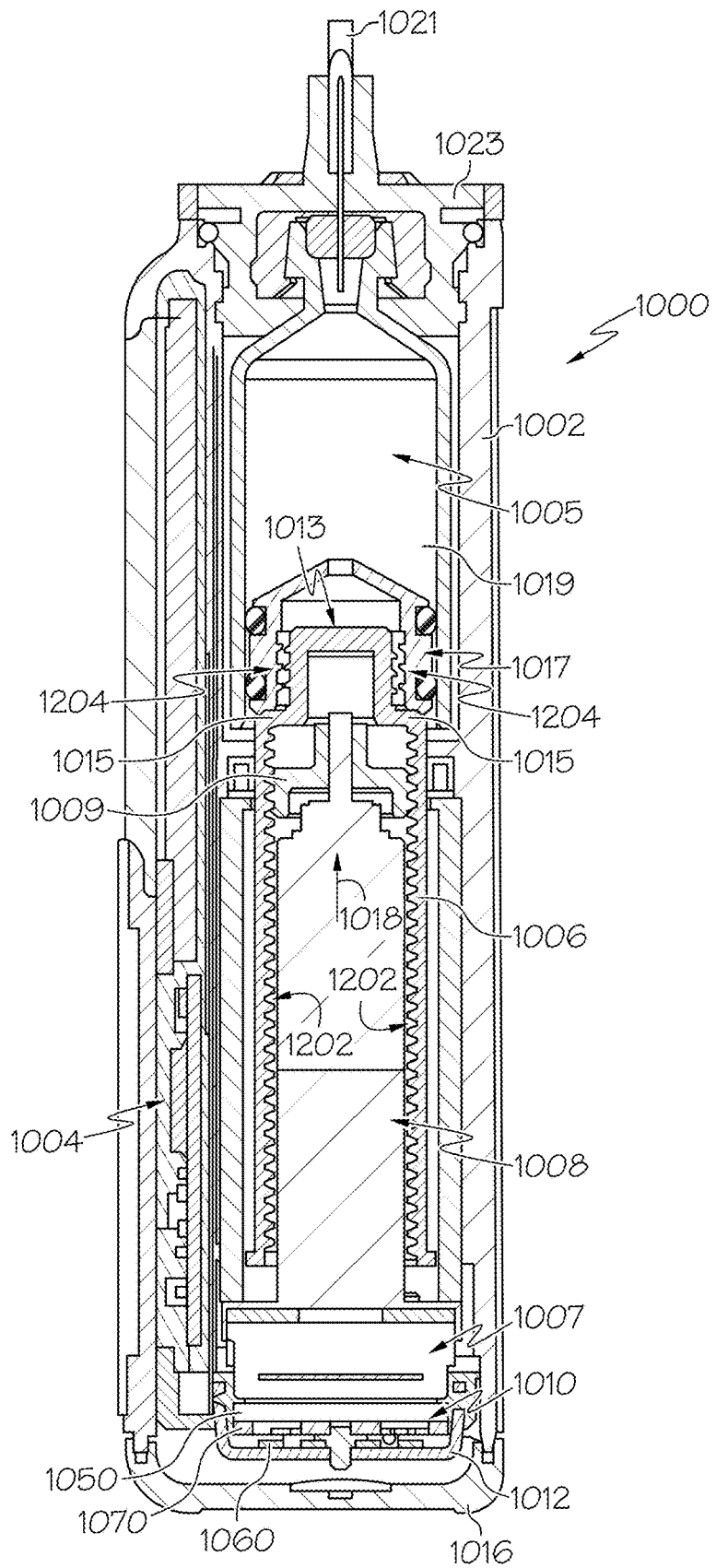
FIG. 12 is a cross-sectional view of the fluid infusion device of FIGS. 10-11 as viewed along line 12-12 in FIG. 11 when assembled with a reservoir inserted in the infusion device.

FIGS. 10-12 depict one exemplary embodiment of a fluid infusion device 1000 (or alternatively, infusion pump) suitable for use in an infusion system, such as, for example, as infusion device 902 in the infusion system 900 of FIG. 9 or as infusion device 102 in the patient management system 100 of FIG. 1. The fluid infusion device 1000 is a portable medical device designed to be carried or worn by a patient (or user), and the fluid infusion device 1000 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 10-12 depict some aspects of the infusion device 1000 in a simplified manner; in practice, the infusion device 1000 could include additional elements, features, or components that are not shown or described in detail herein.

As best illustrated in FIGS. 10-11, the illustrated embodiment of the fluid infusion device 1000 includes a housing 1002 adapted to receive a fluid-containing reservoir 1005. An opening 1020 in the housing 1002 accommodates a fitting 1023 (or cap) for the reservoir 1005, with the fitting 1023 being configured to mate or otherwise interface with tubing 1021 of an infusion set 1025 that provides a fluid path to/from the body of the user. In this manner, fluid communication from the interior of the reservoir 1005 to the user is established via the tubing 1021. The illustrated fluid infusion device 1000 includes a human-machine interface (HMI) 1030 (or user interface) that includes elements 1032, 1034 that can be manipulated by the user to administer a bolus of fluid (e.g., insulin), to change therapy settings, to change user preferences, to select display features, and the like. The infusion device also includes a display element 1026, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 1002 is formed from a substantially rigid material having a hollow interior 1014 adapted to allow an electronics assembly 1004, a sliding member (or slide) 1006, a drive system 1008, a sensor assembly 1010, and a drive system capping member 1012 to be disposed therein in addition to the reservoir 1005, with the contents of the housing 1002 being enclosed by a housing capping member 1016. The opening 1020, the slide 1006, and the drive system 1008 are coaxially aligned in an axial direction (indicated by arrow 1018), whereby the drive system 1008 facilitates linear displacement of the slide 1006 in the axial direction 1018 to dispense fluid from the reservoir 1005 (after the reservoir 1005 has been inserted into opening 1020), with the sensor assembly 1010 being configured to measure axial forces (e.g., forces aligned with the axial direction 1018) exerted on the sensor assembly 1010 responsive to operating the drive system 1008 to displace the slide 1006. In various embodiments, the sensor assembly 1010 may be utilized to detect one or more of the following: an occlusion in a fluid path that slows, prevents, or otherwise degrades fluid delivery from the reservoir 1005 to a user's body; when the reservoir 1005 is empty; when the slide 1006 is properly seated with the reservoir 1005; when a fluid dose has been delivered; when the infusion pump 1000 is subjected to shock or vibration; when the infusion pump 1000 requires maintenance.

Depending on the embodiment, the fluid-containing reservoir 1005 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 11-12, the reservoir 1005 typically includes a reservoir barrel 1019 that contains the fluid and is concentrically and/or coaxially aligned with the slide 1006 (e.g., in the axial direction 1018) when the reservoir 1005 is inserted into the infusion pump 1000. The end of the reservoir 1005 proximate the opening 1020 may include or otherwise mate with the fitting 1023, which secures the reservoir 1005 in the housing 1002 and prevents displacement of the reservoir 1005 in the axial direction 1018 with respect to the housing 1002 after the reservoir 1005 is inserted into the housing 1002. As described above, the fitting 1023 extends from (or through) the opening 1020 of the housing 1002 and mates with tubing 1021 to establish fluid communication from the interior of the reservoir 1005 (e.g., reservoir barrel 1019) to the user via the tubing 1021 and infusion set 1025. The opposing end of the reservoir 1005 proximate the slide 1006 includes a plunger 1017 (or stopper) positioned to push fluid from inside the barrel 1019 of the reservoir 1005 along a fluid path through tubing 1021 to a user. The slide 1006 is configured to mechanically couple or otherwise engage with the plunger 1017, thereby becoming seated with the plunger 1017 and/or reservoir 1005. Fluid is forced from the reservoir 1005 via tubing 1021 as the drive system 1008 is operated to displace the slide 1006 in the axial direction 1018 toward the opening 1020 in the housing 1002.

In the illustrated embodiment of FIGS. 11-12, the drive system 1008 includes a motor assembly 1007 and a drive screw 1009. The motor assembly 1007 includes a motor that is coupled to drive train components of the drive system 1008 that are configured to convert rotational motor motion to a translational displacement of the slide 1006 in the axial direction 1018, and thereby engaging and displacing the plunger 1017 of the reservoir 1005 in the axial direction 1018. In some embodiments, the motor assembly 1007 may also be powered to translate the slide 1006 in the opposing direction (e.g., the direction opposite direction 1018) to retract and/or detach from the reservoir 1005 to allow the reservoir 1005 to be replaced. In exemplary embodiments, the motor assembly 1007 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 1005.

As best shown in FIG. 12, the drive screw 1009 mates with threads 1202 internal to the slide 1006. When the motor assembly 1007 is powered and operated, the drive screw 1009 rotates, and the slide 1006 is forced to translate in the axial direction 1018. In an exemplary embodiment, the infusion pump 1000 includes a sleeve 1011 to prevent the slide 1006 from rotating when the drive screw 1009 of the drive system 1008 rotates. Thus, rotation of the drive screw 1009 causes the slide 1006 to extend or retract relative to the drive motor assembly 1007. When the fluid infusion device is assembled and operational, the slide 1006 contacts the plunger 1017 to engage the reservoir 1005 and control delivery of fluid from the infusion pump 1000. In an exemplary embodiment, the shoulder portion 1015 of the slide 1006 contacts or otherwise engages the plunger 1017 to displace the plunger 1017 in the axial direction 1018. In alternative embodiments, the slide 1006 may include a threaded tip 1013 capable of being detachably engaged with internal threads 1204 on the plunger 1017 of the reservoir 1005, as described in detail in U.S. Pat. Nos. 6,248,093 and 6,485,465, which are incorporated by reference herein.

As illustrated in FIG. 11, the electronics assembly 1004 includes control electronics 1024 coupled to the display element 1026, with the housing 1002 including a transparent window portion 1028 that is aligned with the display element 1026 to allow the display 1026 to be viewed by the user when the electronics assembly 1004 is disposed within the interior 1014 of the housing 1002. The control electronics 1024 generally represent the hardware, firmware, processing logic and/or software (or combinations thereof) configured to control operation of the motor assembly 1007 and/or drive system 1008, as described in greater detail below in the context of FIG. 13. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 1024 includes one or more programmable controllers that may be programmed to control operation of the infusion pump 1000.

The motor assembly 1007 includes one or more electrical leads 1036 adapted to be electrically coupled to the electronics assembly 1004 to establish communication between the control electronics 1024 and the motor assembly 1007. In response to command signals from the control electronics 1024 that operate a motor driver (e.g., a power converter) to regulate the amount of power supplied to the motor from a power supply, the motor actuates the drive train components of the drive system 1008 to displace the slide 1006 in the axial direction 1018 to force fluid from the reservoir 1005 along a fluid path (including tubing 1021 and an infusion set), thereby administering doses of the fluid contained in the reservoir 1005 into the user's body. Preferably, the power supply is realized one or more batteries contained within the housing 1002. Alternatively, the power supply may be a solar panel, capacitor, AC or DC power supplied through a power cord, or the like. In some embodiments, the control electronics 1024 may operate the motor of the motor assembly 1007 and/or drive system 1008 in a stepwise manner, typically on an intermittent basis; to administer discrete precise doses of the fluid to the user according to programmed delivery profiles.

Referring to FIGS. 10-12, as described above, the user interface 1030 includes HMI elements, such as buttons 1032 and a directional pad 1034, that are formed on a graphic keypad overlay 1031 that overlies a keypad assembly 1033, which includes features corresponding to the buttons 1032, directional pad 1034 or other user interface items indicated by the graphic keypad overlay 1031. When assembled, the keypad assembly 1033 is coupled to the control electronics 1024, thereby allowing the HMI elements 1032, 1034 to be manipulated by the user to interact with the control electronics 1024 and control operation of the infusion pump 1000, for example, to administer a bolus of insulin, to change therapy settings, to change user preferences, to select display features, to set or disable alarms and reminders, and the like. In this regard, the control electronics 1024 maintains and/or provides information to the display 1026 regarding program parameters, delivery profiles, pump operation, alarms, warnings, statuses, or the like, which may be adjusted using the HMI elements 1032, 1034. In various embodiments, the HMI elements 1032, 1034 may be realized as physical objects (e.g., buttons, knobs, joysticks, and the like) or virtual objects (e.g., using touch-sensing and/or proximity-sensing technologies). For example, in some embodiments, the display 1026 may be realized as a touch screen or touch-sensitive display, and in such embodiments, the features and/or functionality of the HMI elements 1032, 1034 may be integrated into the display 1026 and the HMI 1030 may not be present. In some embodiments, the electronics assembly 1004 may also include alert generating elements coupled to the control electronics 1024 and suitably configured to generate one or more types of feedback, such as, without limitation: audible feedback; visual feedback; haptic (physical) feedback; or the like.

Referring to FIGS. 11-12, in accordance with one or more embodiments, the sensor assembly 1010 includes a back plate structure 1050 and a loading element 1060. The loading element 1060 is disposed between the capping member 1012 and a beam structure 1070 that includes one or more beams having sensing elements disposed thereon that are influenced by compressive force applied to the sensor assembly 1010 that deflects the one or more beams, as described in greater detail in U.S. Pat. No. 8,474,332, which is incorporated by reference herein. In exemplary embodiments, the back plate structure 1050 is affixed, adhered, mounted, or otherwise mechanically coupled to the bottom surface 1038 of the drive system 1008 such that the back plate structure 1050 resides between the bottom surface 1038 of the drive system 1008 and the housing cap 1016. The drive system capping member 1012 is contoured to accommodate and conform to the bottom of the sensor assembly 1010 and the drive system 1008. The drive system capping member 1012 may be affixed to the interior of the housing 1002 to prevent displacement of the sensor assembly 1010 in the direction opposite the direction of force provided by the drive system 1008 (e.g., the direction opposite direction 1018). Thus, the sensor assembly 1010 is positioned between the motor assembly 1007 and secured by the capping member 1012, which prevents displacement of the sensor assembly 1010 in a downward direction opposite the direction of arrow 1018, such that the sensor assembly 1010 is subjected to a reactionary compressive force when the drive system 1008 and/or motor assembly 1007 is operated to displace the slide 1006 in the axial direction 1018 in opposition to the fluid pressure in the reservoir 1005. Under normal operating conditions, the compressive force applied to the sensor assembly 1010 is correlated with the fluid pressure in the reservoir 1005. As shown, electrical leads 1040 are adapted to electrically couple the sensing elements of the sensor assembly 1010 to the electronics assembly 1004 to establish communication to the control electronics 1024, wherein the control electronics 1024 are configured to measure, receive, or otherwise obtain electrical signals from the sensing elements of the sensor assembly 1010 that are indicative of the force applied by the drive system 1008 in the axial direction 1018.

Figure 13:
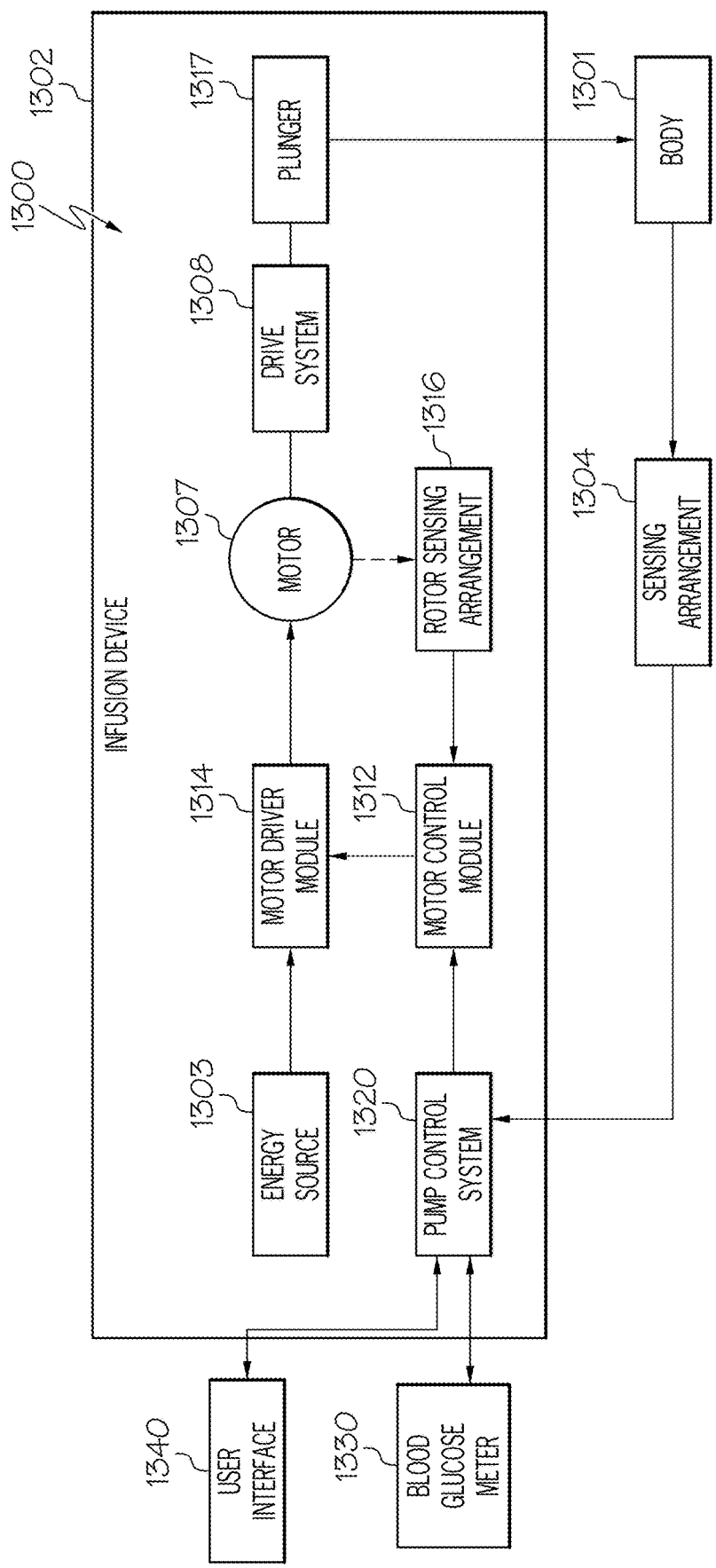
FIG. 13 is a block diagram of an exemplary control system suitable for use in a fluid infusion device in one or more embodiments.

FIG. 13 depicts an exemplary embodiment of a control system 1300 suitable for use with an infusion device 1302, such as any one of the infusion devices 102, 902, 1000 described above. The control system 1300 is capable of controlling or otherwise regulating a physiological condition in the body 1301 of a user to a desired (or target) value or otherwise maintain the condition within a range of acceptable values in an automated or autonomous manner. In one or more exemplary embodiments, the condition being regulated is sensed, detected, measured or otherwise quantified by a sensing arrangement 1304 (e.g., sensing arrangement 904) communicatively coupled to the infusion device 1302. However, it should be noted that in alternative embodiments, the condition being regulated by the control system 1300 may be correlative to the measured values obtained by the sensing arrangement 1304. That said, for clarity and purposes of explanation, the subject matter may be described herein in the context of the sensing arrangement 1304 being realized as a glucose sensing arrangement that senses, detects, measures or otherwise quantifies the user's glucose level, which is being regulated in the body 1301 of the user by the control system 1300.

In exemplary embodiments, the sensing arrangement 1304 includes one or more interstitial glucose sensing elements that generate or otherwise output electrical signals having a signal characteristic that is correlative to, influenced by, or otherwise indicative of the relative interstitial fluid glucose level in the body 1301 of the user. The output electrical signals are filtered or otherwise processed to obtain a measurement value indicative of the user's interstitial fluid glucose level. In exemplary embodiments, a blood glucose meter 1330, such as a finger stick device, is utilized to directly sense, detect, measure or otherwise quantify the blood glucose in the body 1301 of the user. In this regard, the blood glucose meter 1330 outputs or otherwise provides a measured blood glucose value that may be utilized as a reference measurement for calibrating the sensing arrangement 1304 and converting a measurement value indicative of the user's interstitial fluid glucose level into a corresponding calibrated blood glucose value. For purposes of explanation, the calibrated blood glucose value calculated based on the electrical signals output by the sensing element(s) of the sensing arrangement 1304 may alternatively be referred to herein as the sensor glucose value, the sensed glucose value, or variants thereof.

In the illustrated embodiment, the pump control system 1320 generally represents the electronics and other components of the infusion device 1302 that control operation of the fluid infusion device 1302 according to a desired infusion delivery program in a manner that is influenced by the sensed glucose value indicative of a current glucose level in the body 1301 of the user. For example, to support a closed-loop operating mode, the pump control system 1320 maintains, receives, or otherwise obtains a target or commanded glucose value, and automatically generates or otherwise determines dosage commands for operating an actuation arrangement, such as a motor 1307, to displace the plunger 1317 and deliver insulin to the body 1301 of the user based on the difference between a sensed glucose value and the target glucose value. In other operating modes, the pump control system 1320 may generate or otherwise determine dosage commands configured to maintain the sensed glucose value below an upper glucose limit, above a lower glucose limit, or otherwise within a desired range of glucose values. In practice, the infusion device 1302 may store or otherwise maintain the target value, upper and/or lower glucose limit(s), and/or other glucose threshold value(s) in a data storage element accessible to the pump control system 1320.

The target glucose value and other threshold glucose values may be received from an external component (e.g., CCD 906 and/or computing device 908) or be input by a user via a user interface element 1340 associated with the infusion device 1302. In practice, the one or more user interface element(s) 1340 associated with the infusion device 1302 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 1340 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. It should be noted that although FIG. 13 depicts the user interface element(s) 1340 as being separate from the infusion device 1302, in practice, one or more of the user interface element(s) 1340 may be integrated with the infusion device 1302. Furthermore, in some embodiments, one or more user interface element(s) 1340 are integrated with the sensing arrangement 1304 in addition to and/or in alternative to the user interface element(s) 1340 integrated with the infusion device 1302. The user interface element(s) 1340 may be manipulated by the user to operate the infusion device 1302 to deliver correction boluses, adjust target and/or threshold values, modify the delivery control scheme or operating mode, and the like, as desired.

Still referring to FIG. 13, in the illustrated embodiment, the infusion device 1302 includes a motor control module 1312 coupled to a motor 1307 (e.g., motor assembly 1007) that is operable to displace a plunger 1317 (e.g., plunger 1017) in a reservoir (e.g., reservoir 1005) and provide a desired amount of fluid to the body 1301 of a user. In this regard, displacement of the plunger 1317 results in the delivery of a fluid that is capable of influencing the condition in the body 1301 of the user to the body 1301 of the user via a fluid delivery path (e.g., via tubing 1021 of an infusion set 1025). A motor driver module 1314 is coupled between an energy source 1303 and the motor 1307. The motor control module 1312 is coupled to the motor driver module 1314, and the motor control module 1312 generates or otherwise provides command signals that operate the motor driver module 1314 to provide current (or power) from the energy source 1303 to the motor 1307 to displace the plunger 1317 in response to receiving, from a pump control system 1320, a dosage command indicative of the desired amount of fluid to be delivered.

In exemplary embodiments, the energy source 1303 is realized as a battery housed within the infusion device 1302 (e.g., within housing 1002) that provides direct current (DC) power. In this regard, the motor driver module 1314 generally represents the combination of circuitry, hardware and/or other electrical components configured to convert or otherwise transfer DC power provided by the energy source 1303 into alternating electrical signals applied to respective phases of the stator windings of the motor 1307 that result in current flowing through the stator windings that generates a stator magnetic field and causes the rotor of the motor 1307 to rotate. The motor control module 1312 is configured to receive or otherwise obtain a commanded dosage from the pump control system 1320, convert the commanded dosage to a commanded translational displacement of the plunger 1317, and command, signal, or otherwise operate the motor driver module 1314 to cause the rotor of the motor 1307 to rotate by an amount that produces the commanded translational displacement of the plunger 1317. For example, the motor control module 1312 may determine an amount of rotation of the rotor required to produce translational displacement of the plunger 1317 that achieves the commanded dosage received from the pump control system 1320. Based on the current rotational position (or orientation) of the rotor with respect to the stator that is indicated by the output of the rotor sensing arrangement 1316, the motor control module 1312 determines the appropriate sequence of alternating electrical signals to be applied to the respective phases of the stator windings that should rotate the rotor by the determined amount of rotation from its current position (or orientation). In embodiments where the motor 1307 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 1312 operates the motor driver module 1314 to apply the determined alternating electrical signals (e.g., the command signals) to the stator windings of the motor 1307 to achieve the desired delivery of fluid to the user.

When the motor control module 1312 is operating the motor driver module 1314, current flows from the energy source 1303 through the stator windings of the motor 1307 to produce a stator magnetic field that interacts with the rotor magnetic field. In some embodiments, after the motor control module 1312 operates the motor driver module 1314 and/or motor 1307 to achieve the commanded dosage, the motor control module 1312 ceases operating the motor driver module 1314 and/or motor 1307 until a subsequent dosage command is received. In this regard, the motor driver module 1314 and the motor 1307 enter an idle state during which the motor driver module 1314 effectively disconnects or isolates the stator windings of the motor 1307 from the energy source 1303. In other words, current does not flow from the energy source 1303 through the stator windings of the motor 1307 when the motor 1307 is idle, and thus, the motor 1307 does not consume power from the energy source 1303 in the idle state, thereby improving efficiency.

Depending on the embodiment, the motor control module 1312 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 1312 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 1312. The computer-executable programming instructions, when read and executed by the motor control module 1312, cause the motor control module 1312 to perform or otherwise support the tasks, operations, functions, and processes described herein.

It should be appreciated that FIG. 13 is a simplified representation of the infusion device 1302 for purposes of explanation and is not intended to limit the subject matter described herein in any way. In this regard, depending on the embodiment, some features and/or functionality of the sensing arrangement 1304 may implemented by or otherwise integrated into the pump control system 1320, or vice versa. Similarly, in practice, the features and/or functionality of the motor control module 1312 may implemented by or otherwise integrated into the pump control system 1320, or vice versa. Furthermore, the features and/or functionality of the pump control system 1320 may be implemented by control electronics 1024 located in the fluid infusion device 1302, while in alternative embodiments, the pump control system 1320 may be implemented by a remote computing device that is physically distinct and/or separate from the infusion device 1302, such as, for example, the CCD 906 or the computing device 908.

Figure 14:
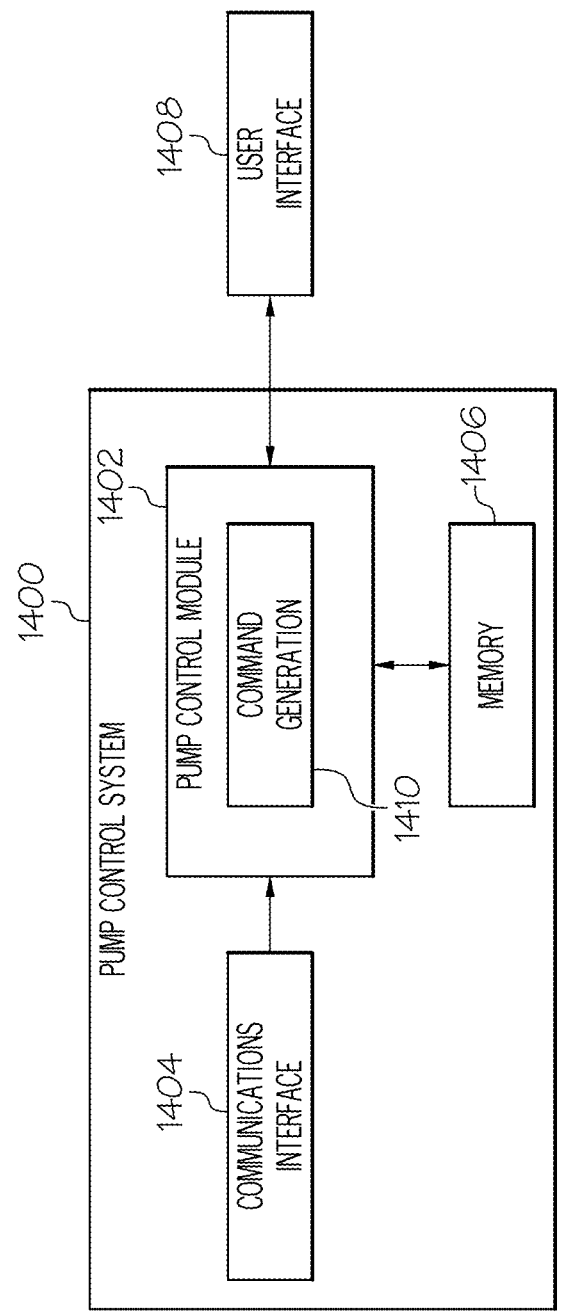
FIG. 14 is a block diagram of an exemplary pump control system suitable for use in the control system of FIG. 13 in one or more embodiments.

FIG. 14 depicts an exemplary embodiment of a pump control system 1400 suitable for use as the pump control system 1320 in FIG. 13 in accordance with one or more embodiments. The illustrated pump control system 1400 includes, without limitation, a pump control module 1402, a communications interface 1404, and a data storage element (or memory) 1406. The pump control module 1402 is coupled to the communications interface 1404 and the memory 1406, and the pump control module 1402 is suitably configured to support the operations, tasks, and/or processes described herein. In exemplary embodiments, the pump control module 1402 is also coupled to one or more user interface elements 1408 (e.g., user interface 1030, 1340) for receiving user input and providing notifications, alerts, or other therapy information to the user. Although FIG. 14 depicts the user interface element 1408 as being separate from the pump control system 1400, in various alternative embodiments, the user interface element 1408 may be integrated with the pump control system 1400 (e.g., as part of the infusion device 1302), the sensing arrangement 1304 or another element of an infusion system 900 (e.g., the computer 908 or CCD 906).

Referring to FIG. 14 and with reference to FIG. 13, the communications interface 1404 generally represents the hardware, circuitry, logic, firmware and/or other components of the pump control system 1400 that are coupled to the pump control module 1402 and configured to support communications between the pump control system 1400 and the sensing arrangement 1304. In this regard, the communications interface 1404 may include or otherwise be coupled to one or more transceiver modules capable of supporting wireless communications between the pump control system 1320, 1400 and the sensing arrangement 1304 or another electronic device 106, 110, 800, 812, 906, 908 in an infusion system 900 or a management system 100, 816. For example, the communications interface 1404 may be utilized to receive sensor measurement values or other measurement data from a sensing arrangement 904, 1304 as well as upload such sensor measurement values to a server 106 or other computing device 110, 800, 812, 908 for purposes of detecting meals or other events and generating reports and related GUI displays as described above. In other embodiments, the communications interface 1404 may be configured to support wired communications to/from the sensing arrangement 1304.

The pump control module 1402 generally represents the hardware, circuitry, logic, firmware and/or other component of the pump control system 1400 that is coupled to the communications interface 1404 and configured to determine dosage commands for operating the motor 1306 to deliver fluid to the body 1301 based on data received from the sensing arrangement 1304 and perform various additional tasks, operations, functions and/or operations described herein. For example, in exemplary embodiments, pump control module 1402 implements or otherwise executes a command generation application 1410 that supports one or more autonomous operating modes and calculates or otherwise determines dosage commands for operating the motor 1306 of the infusion device 1302 in an autonomous operating mode based at least in part on a current measurement value for a condition in the body 1301 of the user. For example, in a closed-loop operating mode, the command generation application 1410 may determine a dosage command for operating the motor 1306 to deliver insulin to the body 1301 of the user based at least in part on the current glucose measurement value most recently received from the sensing arrangement 1304 to regulate the user's blood glucose level to a target reference glucose value. Additionally, the command generation application 1410 may generate dosage commands for boluses that are manually-initiated or otherwise instructed by a user via a user interface element 1408.

Still referring to FIG. 14, depending on the embodiment, the pump control module 1402 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 1402, or in any practical combination thereof. In exemplary embodiments, the pump control module 1402 includes or otherwise accesses the data storage element or memory 1406, which may be realized using any sort of non-transitory computer-readable medium capable of storing programming instructions for execution by the pump control module 1402. The computer-executable programming instructions, when read and executed by the pump control module 1402, cause the pump control module 1402 to implement or otherwise generate the command generation application 1410 and perform tasks, operations, functions, and processes described herein.

It should be understood that FIG. 14 is a simplified representation of a pump control system 1400 for purposes of explanation and is not intended to limit the subject matter described herein in any way. For example, in some embodiments, the features and/or functionality of the motor control module 1312 may be implemented by or otherwise integrated into the pump control system 1400 and/or the pump control module 1402, for example, by the command generation application 1410 converting the dosage command into a corresponding motor command, in which case, the separate motor control module 1312 may be absent from an embodiment of the infusion device 1302.

Figure 15:
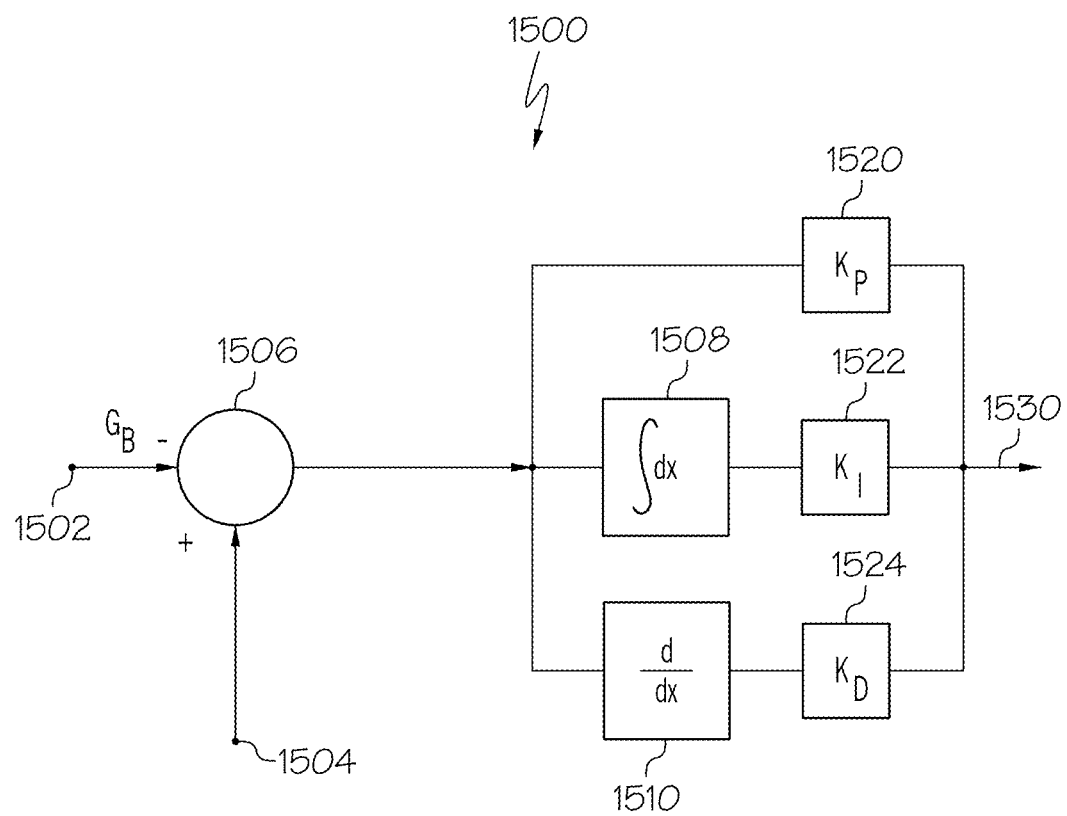
FIG. 15 is a block diagram of a closed-loop control system that may be implemented or otherwise supported by the pump control system in the fluid infusion device of FIG. 13 in one or more exemplary embodiments.

FIG. 15 depicts an exemplary closed-loop control system 1500 that may be implemented by a pump control system 1320, 1400 to provide a closed-loop operating mode that autonomously regulates a condition in the body of a user to a reference (or target) value. It should be appreciated that FIG. 15 is a simplified representation of the control system 1500 for purposes of explanation and is not intended to limit the subject matter described herein in any way.

In exemplary embodiments, the control system 1500 receives or otherwise obtains a target glucose value at input 1502. In some embodiments, the target glucose value may be stored or otherwise maintained by the infusion device 1302 (e.g., in memory 1406), however, in some alternative embodiments, the target value may be received from an external component (e.g., CCD 906 and/or computer 908). In one or more embodiments, the target glucose value may be dynamically calculated or otherwise determined prior to entering the closed-loop operating mode based on one or more patient-specific control parameters. For example, the target blood glucose value may be calculated based at least in part on a patient-specific reference basal rate and a patient-specific daily insulin requirement, which are determined based on historical delivery information over a preceding interval of time (e.g., the amount of insulin delivered over the preceding 24 hours). The control system 1500 also receives or otherwise obtains a current glucose measurement value (e.g., the most recently obtained sensor glucose value) from the sensing arrangement 1304 at input 1504. The illustrated control system 1500 implements or otherwise provides proportional-integral-derivative (PID) control to determine or otherwise generate delivery commands for operating the motor 1310 based at least in part on the difference between the target glucose value and the current glucose measurement value. In this regard, the PID control attempts to minimize the difference between the measured value and the target value, and thereby regulates the measured value to the desired value. PID control parameters are applied to the difference between the target glucose level at input 1502 and the measured glucose level at input 1504 to generate or otherwise determine a dosage (or delivery) command provided at output 1530. Based on that delivery command, the motor control module 1312 operates the motor 1310 to deliver insulin to the body of the user to influence the user's glucose level, and thereby reduce the difference between a subsequently measured glucose level and the target glucose level.

The illustrated control system 1500 includes or otherwise implements a summation block 1506 configured to determine a difference between the target value obtained at input 1502 and the measured value obtained from the sensing arrangement 1304 at input 1504, for example, by subtracting the target value from the measured value. The output of the summation block 1506 represents the difference between the measured and target values, which is then provided to each of a proportional term path, an integral term path, and a derivative term path. The proportional term path includes a gain block 1520 that multiplies the difference by a proportional gain coefficient, $K_P$, to obtain the proportional term. The integral term path includes an integration block 1508 that integrates the difference and a gain block 1522 that multiplies the integrated difference by an integral gain coefficient, $K_I$, to obtain the integral term. The derivative term path includes a derivative block 1510 that determines the derivative of the difference and a gain block 1524 that multiplies the derivative of the difference by a derivative gain coefficient, $K_D$, to obtain the derivative term. The proportional term, the integral term, and the derivative term are then added or otherwise combined to obtain a delivery command that is utilized to operate the motor at output 1530. Various implementation details pertaining to closed-loop PID control and determine gain coefficients are described in greater detail in U.S. Pat. No. 7,402,153, which is incorporated by reference.

In one or more exemplary embodiments, the PID gain coefficients are user-specific (or patient-specific) and dynamically calculated or otherwise determined prior to entering the closed-loop operating mode based on historical insulin delivery information (e.g., amounts and/or timings of previous dosages, historical correction bolus information, or the like), historical sensor measurement values, historical reference blood glucose measurement values, user-reported or user-input events (e.g., meals, exercise, and the like), and the like. In this regard, one or more patient-specific control parameters (e.g., an insulin sensitivity factor, a daily insulin requirement, an insulin limit, a reference basal rate, a reference fasting glucose, an active insulin action duration, pharmodynamical time constants, or the like) may be utilized to compensate, correct, or otherwise adjust the PID gain coefficients to account for various operating conditions experienced and/or exhibited by the infusion device 1302. The PID gain coefficients may be maintained by the memory 1406 accessible to the pump control module 1402. In this regard, the memory 1406 may include a plurality of registers associated with the control parameters for the PID control. For example, a first parameter register may store the target glucose value and be accessed by or otherwise coupled to the summation block 1506 at input 1502, and similarly, a second parameter register accessed by the proportional gain block 1520 may store the proportional gain coefficient, a third parameter register accessed by the integration gain block 1522 may store the integration gain coefficient, and a fourth parameter register accessed by the derivative gain block 1524 may store the derivative gain coefficient.

Referring to FIGS. 13-15, in one or more embodiments, the patient-specific meal detection model may be stored or otherwise maintained by the pump control system 1320, 1400 (e.g., in memory 1406) to support the infusion device 1302 performing the meal detection process 600 substantially in real-time. In this regard, the pump control system 1320, 1400 may continually monitor the sensor glucose measurement values received from the sensing arrangement 1304 and apply the meal detection model to the most recent set of sensor glucose measurement values (e.g., buffered sensor glucose measurements corresponding to the preceding hour) to detect or otherwise identify whether the sensor glucose measurements indicate that the patient has consumed a meal. In response to detecting a meal, the pump control system 1320, 1400 may tag, mark, or otherwise provide an indication associated with one or more sensor glucose measurement values prior to uploading the sensor glucose measurement values to a server (e.g., server 106). Additionally, in some embodiments, the pump control system 1320, 1400 may automatically adjust one or more aspects of the autonomous operation of the infusion device 1302 to temporarily modify delivery of the infusion device 1302 to account for the patient consuming a meal. For example, one or more of the closed-loop gain coefficients 1520, 1522, 1524 may be temporarily modified to alter the response of the closed-loop control system 1500 in a manner that more effectively regulates or moderates the patient's glucose level after consuming a meal (e.g., to prevent a postprandial hyperglycemic or hypoglycemic event). In this regard, it should be appreciated that the patient-specific meal detection models may be employed in any number of different ways depending on the needs of a particular application, and the subject matter described herein is not limited to any particular implementation described herein.

It should be noted that although the subject matter may be described herein primarily in the context of an infusion device delivering insulin to the body of a patient with diabetes to regulate the patient's glucose level for purposes of explanation, in practice, the subject matter is not limited to use with infusion devices, insulin, diabetes or glucose control, and the like. Rather, the subject matter may be implemented in an equivalent manner in the context of patient management systems that do not include an infusion device, for example, in systems with where patients self-administer injections, oral medications, or the like, in systems where a sensing arrangement is utilized to monitor any a physiological condition of a patient in a substantially continuous manner, or in the context of a patient with dysglycemia or another physiological condition being monitored that is influenced by meals or other behavioral events.

For the sake of brevity, conventional techniques related to glucose sensing and/or monitoring, bolusing, meal boluses or correction boluses, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not necessarily limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A processor-implemented method comprising:
    obtaining a plurality of glucose measurements indicative of a glucose level in a body of a patient during an analysis interval;
    determining one or more glucose measurement statistics based on the plurality of glucose measurements that are correlative to an occurrence of a meal for the patient;
    determining a likelihood of the patient having consumed a meal during the analysis interval based on the one or more glucose measurement statistics; and
    detecting the occurrence of the meal during the analysis interval based on the likelihood of the patient having consumed the meal during the analysis interval.

2. The method of claim 1, wherein determining the likelihood of the patient having consumed the meal during the analysis interval is based on historical event data associated with the patient.

3. The method of claim 2, wherein the historical event data comprises meal bolus data associated with the patient, and wherein determining the likelihood is based on the meal bolus data associated with the patient.

4. The method of claim 1, further comprising:
    determining respective correlation coefficient values for the one or more glucose measurement statistics using a patient-specific meal detection model,
    wherein determining the likelihood of the patient having consumed the meal during the analysis interval is based on the values for the one or more glucose measurement statistics and the respective correlation coefficient values for the one or more glucose measurements statistics.

5. The method of claim 1, further comprising determining whether a meal bolus was identified and/or delivered during the analysis interval.

6. The method of claim 1, further comprising providing an indication of the occurrence of the meal during the analysis interval.

7. The method of claim 1, wherein the detected occurrence of the meal corresponds to detection of an unannounced meal.

8. The method of claim 1, further comprising updating historical event data associated with the patient to indicate the occurrence of the meal associated with the analysis interval.

9. The method of claim 1, wherein the one or more glucose measurement statistics are particular to the patient and have been identified as correlative of meal consumption for the patient.

10. The method of claim 1, wherein the one or more glucose measurement statistics comprise at least a mean or average rate of change of the plurality of glucose measurements over at least a portion of the analysis interval.

11. A system comprising:
    one or more processors; and
    one or more processor-readable storage media storing instructions which, when executed by the one or more processors, cause performance of:
        obtaining a plurality of glucose measurements indicative of a glucose level in a body of a patient during an analysis interval;
        determining one or more glucose measurement statistics based on the plurality of glucose measurements that are correlative to an occurrence of a meal for the patient;
        determining a likelihood of the patient having consumed a meal during the analysis interval based on the one or more glucose measurement statistics; and
        detecting the occurrence of the meal during the analysis interval based on the likelihood of the patient having consumed the meal during the analysis interval.

12. The system of claim 11, wherein determining the likelihood of the patient having consumed the meal during the analysis interval is based on historical event data associated with the patient.

13. The system of claim 12, wherein the historical event data comprises meal bolus data associated with the patient, and wherein determining the likelihood is based on the meal bolus data associated with the patient.

14. The system of claim 11, wherein the instructions further cause performance of:
   determining respective correlation coefficient values for the one or more glucose measurement statistics using a patient-specific meal detection model,
   wherein determining the likelihood of the patient having consumed the meal during the analysis interval is based on the values for the one or more glucose measurement statistics and the respective correlation coefficient values for the one or more glucose measurements statistics.

15. The system of claim 11, wherein the instructions further cause performance of determining whether a meal bolus was identified and/or delivered during the analysis interval.

16. The system of claim 11, wherein the instructions further cause performance of providing an indication of the occurrence of the meal during the analysis interval.

17. The system of claim 11, wherein the detected occurrence of the meal corresponds to detection of an unannounced meal.

18. The system of claim 11, wherein the instructions further cause performance of updating historical event data associated with the patient to indicate the occurrence of the meal associated with the analysis interval.

19. A processor-implemented method comprising:
   obtaining a plurality of glucose measurements indicative of a glucose level in a body of a patient during an analysis interval;
   determining one or more glucose measurement statistics based on the plurality of glucose measurements;
   determining a likelihood of the patient having consumed a meal during the analysis interval using a patient-specific meal detection model and the one or more glucose measurement statistics; and
   detecting an occurrence of the meal during the analysis interval based on the likelihood of the patient having consumed the meal during the analysis interval.

20. The method of claim 19, wherein the patient-specific meal detection model is generated using time segments of historical data classified as corresponding to meal consumption or no meal consumption and corresponding glucose statistics for the time segments.

\* \* \* \* \*